United States Patent
Suragani et al.

(10) Patent No.: US 12,145,970 B2
(45) Date of Patent: Nov. 19, 2024

(54) TWISTED GASTRULATION POLYPEPTIDES AND USES THEREOF

(71) Applicant: ACCELERON PHARMA INC., Cambridge, MA (US)

(72) Inventors: Rajasekhar Naga Venkata Sai Suragani, Wrentham, MA (US); Asya Grinberg, Lexington, MA (US); Dianne Sako, Medford, MA (US)

(73) Assignee: ACCELERON PHARMA INC., Cambridge, MA (US)

(*) Notice: Subject to any disclaimer, the term of this patent is extended or adjusted under 35 U.S.C. 154(b) by 0 days.

(21) Appl. No.: 18/175,163

(22) Filed: Feb. 27, 2023

(65) Prior Publication Data
US 2023/0234998 A1     Jul. 27, 2023

Related U.S. Application Data

(62) Division of application No. 16/332,724, filed as application No. PCT/US2017/051727 on Sep. 15, 2017, now abandoned.

(60) Provisional application No. 62/395,088, filed on Sep. 15, 2016.

(51) Int. Cl.
| | |
|---|---|
| *A61K 38/17* | (2006.01) |
| *A61K 45/06* | (2006.01) |
| *A61P 7/06* | (2006.01) |
| *C07K 14/47* | (2006.01) |
| *C07K 14/52* | (2006.01) |
| *C07K 19/00* | (2006.01) |
| *A61K 38/00* | (2006.01) |

(52) U.S. Cl.
CPC .......... *C07K 14/4703* (2013.01); *A61K 38/17* (2013.01); *A61K 45/06* (2013.01); *A61P 7/06* (2018.01); *C07K 14/52* (2013.01); *C07K 19/00* (2013.01); *A61K 38/00* (2013.01); *C07K 2319/30* (2013.01)

(58) Field of Classification Search
CPC .................. A61K 38/17; C07K 14/47
See application file for complete search history.

(56) References Cited

U.S. PATENT DOCUMENTS

| | | | |
|---|---|---|---|
| 5,519,115 A | 5/1996 | Mapelli et al. | |
| 8,338,377 B2 * | 12/2012 | Seehra | A61P 35/04 |
| | | | 435/69.7 |
| 2006/0276385 A1 | 12/2006 | Jo | |
| 2008/0119396 A1 | 5/2008 | Knopf et al. | |
| 2008/0293077 A1 * | 11/2008 | Holtzman | C07K 14/52 |
| | | | 435/375 |
| 2008/0300188 A1 | 12/2008 | Yang et al. | |

FOREIGN PATENT DOCUMENTS

| | | |
|---|---|---|
| CA | 2650229 A1 | 11/2007 |
| CA | 2890733 A1 | 5/2014 |
| CA | 2942954 A1 | 9/2015 |
| WO | 1998046641 A1 | 10/1998 |
| WO | 2013186777 A2 | 12/2013 |
| WO | 2014152940 A1 | 9/2014 |

OTHER PUBLICATIONS

Oelgeschläger et al., Development, 2003, vol. 130(17): 4047-4056.*
Billington Charles J. Jr., et al., Glycosylation of Twisted gastrulation is required for BMP binding and activity during craniofacial development, Frontiers in Physiology, 2011, 1-9, vol. 2 | Article 59.
Chang, et al., Twisted gastrulation can function as a BPM antagonist, Nature, 2001, 483-487, 410(6827).
Czajkowsky, Daniel M. et al., Fc-fusion proteins: new developments and future perspectives, EMBO Mol Med, 2012, 1015-1028, 4.
Extended European Search Report for EP Application No. EP 17851586 dated Mar. 17, 2020, 12 pages.
Gardenghi, Sara et al., Hepcidin as a therapeutic tool to limit iron overload and improve anemia in β-thalassemic mice, J Clin Invest, 2010, 4466-4477, 120.
Gen Bank: AEV43323.1, Fe IgG1 heavy chain constant region, partial [*Homo sapiens*] Jul. 25, 2016, 1 page.
Graf, Daniel et al., Evolutionary conservation, developmental expression, and genomic mapping of n1annnalian Twisted gastrulation, Mammalian Genome, 2001, 554-560, 12.
Huntley, Raphael et al., The function of Twisted Gastrulation in regulating osteoclast differentiation is dependent on BMP binding, Journal of Cellular Biochemistry, 2016, 2239-2246, 116.
International Search Report for International Application No. PCT/US2017/051727 dated Dec. 28, 2017, 7 pages.
Kautz, Leon et al., Molecular liaisons between erythropoiesis and iron metabolism, Blood, 2014, 479-482, 124:4.
Lo, Kin-Ming et al., High level expression and secretion of Fc-X fusion proteins in mammalian cells, Protein Engineering, 1998, 495-500, 11:6.

(Continued)

*Primary Examiner* — Xiaozhen Xie

(74) *Attorney, Agent, or Firm* — Su Kyung Suh; Anna L. Cocuzzo

(57) ABSTRACT

In certain aspects, the present invention provides compositions and methods for altering iron metabolism to increase red blood cell and/or hemoglobin levels in vertebrates, including rodents and primates, and particularly in humans.

12 Claims, 7 Drawing Sheets

Specification includes a Sequence Listing.

(56) References Cited

OTHER PUBLICATIONS

Mirciov, Cornel S. G. et al., Characterization of Putative Erythroid Regulators of Hepcidin in Mouse Models of Anemia, PLoS ONE, 2017, 1-17, 12(1): e0171054.

NCBI Reference Sequence: NP_065699.1, Twisted gastrulation protein homolog 1 precursor [*Homo sapiens*] Sep. 10, 2017, 3 pages.

Nosaka, Tetsuya et al., Mammalian Twisted Gastrulation Is Essential for Skeleto-Lymphogenesis, Molecular and Cellular Biology, 2003, 2969-2980, 23:8.

Tanno, Toshhiko et al., Identification of TWSG1 as a second novel erythroid regulator of hepcidin expression in murine and human cells, Blood, 2009, 181-186, 114(1).

Tanno, Toshihiko et al., Iron Loading and Overloading due to Ineffective Erythropoiesis, Advances in Hematology, 2010, 1-8, vol. 2010 | Article ID 358283.

\* cited by examiner

```
  1  CNKALCASDV  SKCLIQELCQ  CRPGEGNCSC  CKECMLCLGA  LWDECCDCVG
 51  MCNPRNYSDT  PPTSKSTVEE  LHEPIPSLFR  ALTEGDTQLN  WNIVSFPVAE
101  ELSHHENLVS  FLETVNQPHH  QNVSVPSNNV  HAPYSSDKEH  MCTVVYFDDC
151  MSIHQCKISC  ESMGASKYRW  FHNACCECIG  PECIDYGSKT  VKCMNCMF
     (SEQ ID NO: 8)
```

Figure 1

```
  1  CNKALCASDV  SKCLIQELCQ  CRPGEGNCSC  CKECMLCLGA  LWDECCDCVG
 51  MCNPRNYSDT  PPTSKSTVEE  LHEPIPSLFR  ALTEGDTQLN  WNIVSFPVAE
101  ELSHHENLVS  FLETVNQPHH  QNVSVPSNNV  HAPYSSDKEH  MCTVVYFDDC
151  MSIHQCKISC  ESMGASKYRW  FHNACCECIG  PECIDYGSKT  VKCMNCMFTG
201  GGTHTCPPCP  APELLGGPSV  FLFPPKPKDT  LMISRTPEVT  CVVVDVSHED
251  PEVKFNWYVD  GVEVHNAKTK  PREEQYNSTY  RVVSVLTVLH  QDWLNGKEYK
301  CKVSNKALPA  PIEKTISKAK  GQPREPQVYT  LPPSREEMTK  NQVSLTCLVK
351  GFYPSDIAVE  WESNGQPENN  YKTTPPVLDS  DGSFFLYSKL  TVDKSRWQQG
401  NVFSCSVMHE  ALHNHYTQKS  LSLSPGK     (SEQ ID NO: 9)
```

Figure 2

| | |
|---|---|
| 1 | MDAMKRGLCC VLLLCGAVFV SPGASCNKAL CASDVSKCLI QELCQCRPGE |
| 51 | GNCSCCKECM LCLGALWDEC CDCVGMCNPR NYSDTPPTSK STVEELHEPI |
| 101 | PSLFRALTEG DTQLNWNIVS FPVAEELSHH ENLVSFLETV NQPHHQNVSV |
| 151 | PSNNVHAPYS SDKEHMCTVV YFDDCMSIHQ CKISCESMGA SKYRWFHNAC |
| 201 | CECIGPECID YGSKTVKCMN CMFTGGGTHT CPPCPAPELL GGPSVFLFPP |
| 251 | KPKDTLMISR TPEVTCVVVD VSHEDPEVKF NWYVDGVEVH NAKTKPREEQ |
| 301 | YNSTYRVVSV LTVLHQDWLN GKEYKCKVSN KALPAPIEKT ISKAKGQPRE |
| 351 | PQVYTLPPSR EEMTKNQVSL TCLVKGFYPS DIAVEWESNG QPENNYKTTP |
| 401 | PVLDSDGSFF LYSKLTVDKS RWQQGNVFSC SVMHEALHNH YTQKSLSLSP |
| 451 | GK (SEQ ID NO: 13) |

Figure 3

```
   1  ATGGATGCAA TGAAGAGAGG GCTCTGCTGT GTGCTGCTGC TGTGTGGAGC
  51  AGTCTTCGTT TCGCCCGGCG CCAGCTGTAA CAAAGCACTC TGTGCTAGTG
 101  ATGTGAGCAA ATGCCTCATT CAGGAGCTCT GCCAGTGCCG GCCGGGAGAA
 151  GGCAATTGCT CCTGCTGTAA GGAGTGCATG CTGTGTCTTG GGCCCTTTG
 201  GGACGAGTGC TGTGACTGTG TTGGTATGTG TAATCCTCGA AATTATAGTG
 251  ACACACCTCC AACTTCAAAG AGCACAGTGG AGGAGCTGCA TGAACCGATC
 301  CCTTCTCTCT TCCGGGCACT CACAGAAGGA GATACTCAGT TGAATTGGAA
 351  CATCGTTTCT TTCCTGTTG CAGAAGAACT TTCACATCAT GAGAATCTGG
 401  TTTCATTTTT AGAAACTGTG AACCAGCCAC ACCACCAGAA TGTGTCTGTC
 451  CCCAGCAATA ATGTTCACGC GCCTTATTCC AGTGACAAAG AACACATGTG
 501  TACTGTGGTT TATTTTGATG ACTGCATGTC CATACATCAG TGTAAAATAT
 551  CCTGTGAGTC CATGGGAGCA TCCAAATATC GCTGGTTTCA TAATGCCTGC
 601  TGCGAGTGCA TTGGTCCAGA ATGTATTGAC TATGGTAGTA AAACTGTCAA
 651  ATGTATGAAC TGCATGTTTA CCGGTGGTGG AACTCACACA TGCCCACCGT
 701  GCCCAGCACC TGAACTCCTG GGGGACCGT CAGTCTTCCT CTTCCCCCCA
 751  AAACCCAAGG ACACCCTCAT GATCTCCCGG ACCCCTGAGG TCACATGCGT
 801  GGTGGTGGAC GTGAGCCACG AAGACCCTGA GGTCAAGTTC AACTGGTACG
 851  TGGACGGCGT GGAGGTGCAT AATGCCAAGA CAAAGCCGCG GGAGGAGCAG
 901  TACAACAGCA CGTACCGTGT GGTCAGCGTC CTCACCGTCC TGCACCAGGA
 951  CTGGCTGAAT GGCAAGGAGT ACAAGTGCAA GGTCTCCAAC AAAGCCCTCC
1001  CAGCCCCCAT CGAGAAAACC ATCTCCAAAG CCAAAGGGCA GCCCCGAGAA
1051  CCACAGGTGT ACACCCTGCC CCCATCCCGG GAGGAGATGA CCAAGAACCA
1101  GGTCAGCCTG ACCTGCCTGG TCAAAGGCTT CTATCCCAGC GACATCGCCG
1151  TGGAGTGGGA GAGCAATGGG CAGCCGGAGA ACAACTACAA GACCACGCCT
1201  CCCGTGCTGG ACTCCGACGG CTCCTTCTTC CTCTATAGCA AGCTCACCGT
1251  GGACAAGAGC AGGTGGCAGC AGGGGAACGT CTTCTCATGC TCCGTGATGC
1301  ATGAGGCTCT GCACAACCAC TACACGCAGA AGAGCCTCTC CCTGTCTCCG
1351  GGTAAA              (SEQ ID NO: 14)
```

Figure 4

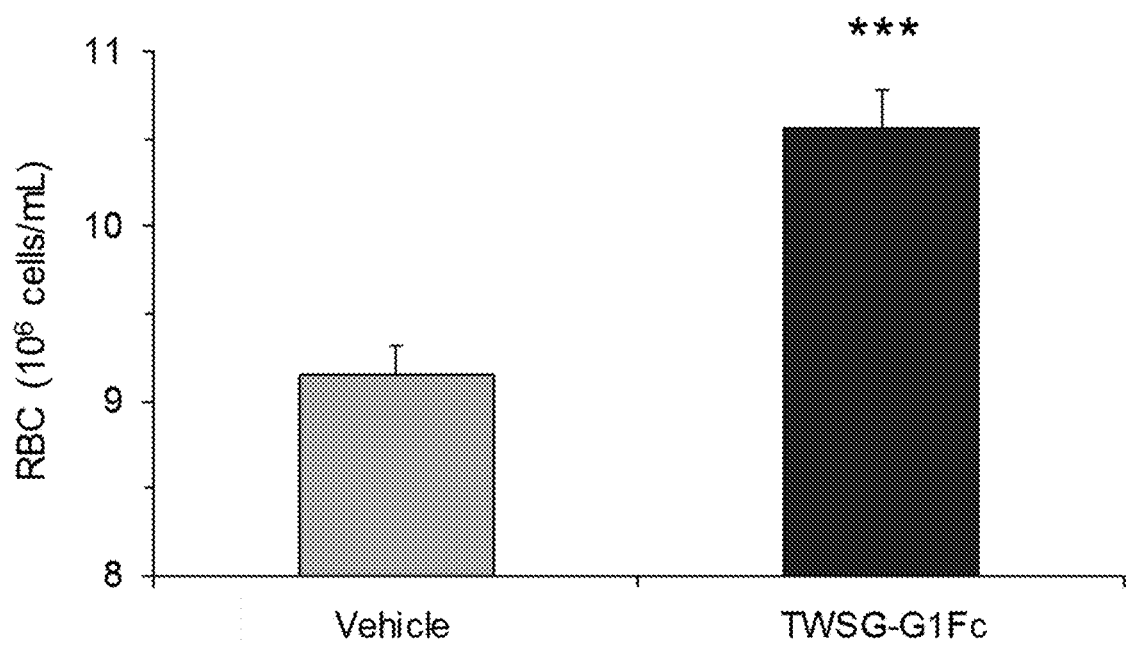
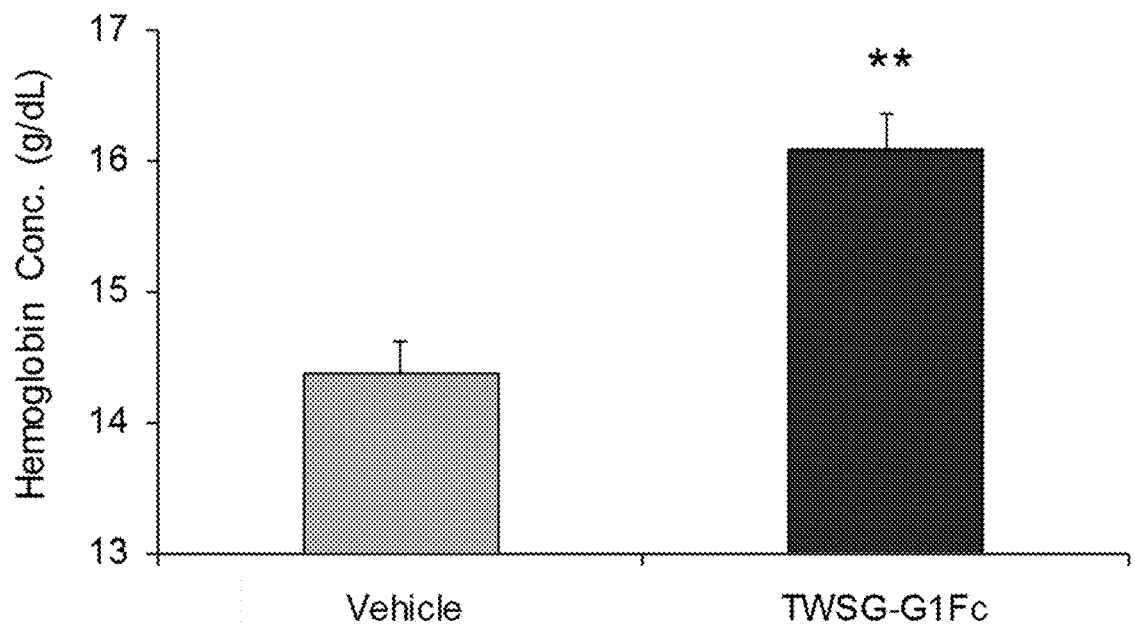
Figure 7

TWISTED GASTRULATION POLYPEPTIDES AND USES THEREOF

RELATED APPLICATIONS

This application is a divisional application of U.S. patent application Ser. No. 16/332,724, filed Mar. 12, 2019 (now abandoned), which is a national-phase application of International Application No. PCT/US2017/051727, filed Sep. 15, 2017, which claims the benefit of priority to U.S. Provisional Patent Application Ser. No. 62/395,088, filed Sep. 15, 2016. The entire contents of these applications are hereby incorporated by reference in their entireties.

SEQUENCE LISTING

The instant application contains a Sequence Listing which has been submitted electronically XML format and is hereby incorporated by reference in its entirety. Said Sequence Listing was created on Feb. 27, 2023, has the filename 25470-US-DIV.xml, and is 27,254 bytes in size.

BACKGROUND OF THE INVENTION

The mature red blood cell (RBC), or erythrocyte, is responsible for oxygen transport in the circulatory systems of vertebrates. Red blood cells contain high concentrations of hemoglobin, a protein that binds oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways controls the balance of cell proliferation, differentiation, survival and death. Under normal conditions, red blood cells are produced at a rate that maintains a constant red cell mass in the body, and the rate may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (EPO) is widely recognized as the most significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Effects of EPO are mediated by a cell-surface receptor belonging to the cytokine receptor superfamily. The human EPO receptor gene encodes a 483 amino-acid transmembrane protein, whereas the active EPO receptor is thought to exist as a multimeric complex even in the absence of ligand (See U.S. Pat. No. 6,319,499). The cloned full-length EPO receptor expressed in mammalian cells binds EPO with an affinity similar to that of the native receptor on erythroid progenitor cells. Binding of EPO to its receptor causes a conformational change resulting in receptor activation and biological effects including increased proliferation of immature erythroblasts, increased differentiation of immature erythroblasts, and decreased apoptosis in erythroid progenitor cells (Liboi et al., 1993, Proc Natl Acad Sci USA 90:11351-11355; Koury et al., 1990, Science 248:378-381).

Various forms of recombinant EPO are used by physicians to increase red blood cell levels in a variety of clinical settings, and particularly for the treatment of anemia. Anemia is a broadly-defined condition characterized by lower than normal levels of hemoglobin or red blood cells in the blood. In some instances, anemia is caused by a primary disorder in the production or survival of red blood cells. More commonly, anemia is secondary to diseases of other systems (Weatherall & Provan, 2000, Lancet 355, 1169-1175). Anemia may result from a reduced rate of production or increased rate of destruction of red blood cells or by loss of red blood cells due to bleeding. Anemia may result from a variety of disorders that include, for example, chronic renal failure, chemotherapy treatment, myelodysplastic syndrome, rheumatoid arthritis, and bone marrow transplantation.

Treatment with EPO typically causes a rise in hemoglobins by about 1-3 g/dL in healthy humans over a period of weeks. When administered to anemic individuals, this treatment regimen often provides substantial increases in hemoglobin and red blood cell levels and leads to improvements in quality of life and prolonged survival. EPO is not uniformly effective, and many individuals are refractory to even high doses (Horl et al., 2000, Nephrol Dial Transplant 15, 43-50). Over 50% of patients with cancer have an inadequate response to EPO, approximately 10% with end-stage renal disease are hyporesponsive (Glaspy et al., 1997, J Clin Oncol 15, 1218-1234; Demetri et al., 1998, J Clin Oncol 16, 3412-3425), and less than 10% with myelodysplastic syndrome respond favorably (Estey, 2003, Curr Opin Hematol 10, 60-67). Several factors, including inflammation, iron and vitamin deficiency, inadequate dialysis, aluminum toxicity, and hyperparathyroidism may predict a poor therapeutic response. The molecular mechanisms of resistance to EPO are as yet unclear. Recent evidence suggests that higher doses of EPO may be associated with an increased risk of cardiovascular morbidity, tumor growth, and mortality in some patient populations (Krapf et al., 2009, Clin J Am Soc Nephrol 4:470-480; Glaspy, 2009, Annu Rev Med 60:181-192). It has therefore been recommended that EPO-based therapeutic compounds (erythropoietin-stimulating agents, ESAs) be administered at the lowest dose sufficient to avoid the need for red blood cell transfusions (Jelkmann et al., 2008, Crit Rev Oncol. Hematol 67:39-61).

Thus, there is a need for alternative methods for increasing numbers of red blood cells and levels of iron available for erythropoiesis in the context of anemia of inflammation.

SUMMARY OF THE INVENTION

In one aspect, the present disclosure provides novel Twisted gastrulation (TWSG) polypeptides comprising, e.g., an isolated TWSG polypeptide, a soluble TWSG polypeptide, or an at least partly purified TWSG polypeptide. In some embodiments, the present disclosure provides an isolated, soluble, and at least partly purified TWSG polypeptide.

In some embodiments, the present disclosure provides a polypeptide comprising a TWSG polypeptide and another polypeptide, e.g., a polypeptide heterologous to the TWSG polypeptide. In some embodiments, the heterologous polypeptide is a fragment crystallizable region (Fc) polypeptide. The polypeptide may be, for example, a fusion protein comprising a TWSG polypeptide and an Fc polypeptide.

In some embodiments, the TWSG polypeptide is a human or non-human vertebrate TWSG polypeptide, or a chimeric TWSG polypeptide comprising at least part of a human TWSG polypeptide and at least part of a non-human vertebrate TWSG polypeptide. Representative non-human vertebrates include, for example, non-human mammals, such as a non-human primate, a mouse, a rat, a rabbit, a dog, a cat, a pig, a sheep, a cow, a horse, a donkey, a camel, etc., and non-human non-mammal vertebrates (e.g., chicken, snake, etc.). Non-human primates include, for example, a monkey, a chimpanzee, a gibbon, a macaque, a gorilla, an orangutan, etc.

In certain embodiments, the TWSG polypeptide of the present disclosure is encodable by a polynucleotide comprising a nucleic acid sequence at least about 60, 65, 70, 75, 80, 85, 90, 91, 92, 93, 94, 95, 96, 97, 98, 99, or 100% identical to the sequence of SEQ ID NO: 2.

In some embodiments, the TWSG polypeptide is encodable by a polynucleotide comprising a nucleic acid sequence of SEQ ID NO: 2. In some embodiments, the TWSG polypeptide is encodable by a polynucleotide that hybridizes, e.g., under highly stringent conditions, to a nucleic acid sequence that is complementary to the sequence of SEQ ID NO: 2. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In certain embodiments, the TWSG polypeptide of the present disclosure comprises an amino acid sequence at least about 60, 65, 70, 75, 80, 85, 90, 91, 92, 93, 94, 95, 96, 97, 98, 99, or 100% identical to the sequence of SEQ ID NO: 8. In some embodiments, the TWSG polypeptide comprises an amino acid sequence at least 80% identical to the sequence of SEQ ID NO: 8. In some embodiments, the TWSG polypeptide comprises an amino acid sequence at least 85% identical to the sequence of SEQ ID NO: 8. In some embodiments, the TWSG polypeptide comprises an amino acid sequence at least 90% identical to the sequence of SEQ ID NO: 8. In some embodiments, the TWSG polypeptide comprises an amino acid sequence at least 95% identical to the sequence of SEQ ID NO: 8. In some embodiments, the TWSG polypeptide comprises an amino acid sequence at least 99% identical to the sequence of SEQ ID NO: 8. In some embodiments, the TWSG polypeptide comprises an amino acid sequence of SEQ ID NO: 8.

In some embodiments, the TWSG polypeptide of the present disclosure is a wild-type or naturally occurring TWSG polypeptide. In other embodiments, the TWSG polypeptide comprises at least one amino acid substitution relative to a wild-type or naturally occurring sequence. Such amino acid substitution may be, for example, in a potential glycosylation site in order to, for example, remove a potential glycosylation site. Such amino acid substitution may be, for example, in a site potentially affecting the biological function and/or interaction affinity of the TWSG polypeptide.

In some embodiments, the TWSG polypeptide comprises a signal sequence. Such signal sequence may be at, e.g., the N-terminus of the TWSG polypeptide. In other embodiments, the TWSG polypeptide does not comprise a signal sequence.

In some embodiments, the Fc polypeptide is a human or non-human vertebrate Fc polypeptide. Such non-human vertebrate may be, for example, a non-human mammal, including, for example, a non-human primate. The Fc polypeptide may be derived from an IgG protein, such as IgG1, IgG2, IgG3, IgG4, or a chimeric IgG subclass (e.g., IgG2/G4). In some embodiments, the Fc polypeptide is derived from IgG1.

In some embodiments, the Fc polypeptide is encodable by a polynucleotide that hybridizes, e.g., under highly stringent conditions, to a nucleic acid sequence that is complementary to the sequence of a polynucleotide encoding a polypeptide comprising an amino acid sequence of SEQ ID NO: 3, 4, 5, 6, or 7. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

The Fc polypeptide may comprise an amino acid sequence at least about 60, 65, 70, 75, 80, 85, 90, 91, 92, 93, 94, 95, 96, 97, 98, 99, or 100% identical to the sequence of SEQ ID NO: 3, 4, 5, 6, or 7. In some embodiments, the Fc polypeptide comprises an amino acid sequence at least 80% identical to the sequence of SEQ ID NO: 3, 4, 5, 6, or 7. In some embodiments, the Fc polypeptide comprises an amino acid sequence at least 85% identical to the sequence of SEQ ID NO: 3, 4, 5, 6, or 7. In some embodiments, the Fc polypeptide comprises an amino acid sequence at least 90% identical to the sequence of SEQ ID NO: 3, 4, 5, 6, or 7. In some embodiments, the Fc polypeptide comprises an amino acid sequence at least 95% identical to the sequence of SEQ ID NO: 3, 4, 5, 6, or 7. In some embodiments, the Fc polypeptide comprises an amino acid sequence at least 99% identical to the sequence of SEQ ID NO: 3, 4, 5, 6, or 7. In some embodiments, the Fc polypeptide comprises an amino acid sequence of SEQ ID NO: 3, 4, 5, 6, or 7.

In some embodiments, the Fc polypeptide is a wild-type or naturally occurring Fc polypeptide. In other embodiments, the Fc polypeptide comprises at least one amino acid substitution relative to a wild-type or naturally occurring sequence. Such amino acid substitution may be, for example, in a potential glycosylation site in order to, for example, remove a potential glycosylation site. Such amino acid substitution may be, for example, in a site potentially affecting the biological function and/or interaction affinity of the Fc polypeptide.

The polypeptide of the present disclosure may be a fusion protein comprising a TWSG polypeptide and a Fc polypeptide. In such embodiments, the C-terminus of TWSG polypeptide may be fused to the N-terminus of the Fc polypeptide. In other such embodiments, the C-terminus of the Fc polypeptide may be fused to the N-terminus of the TWSG polypeptide. Such fusion proteins, regardless of the order of these elements, are collectively referred to herein as "TWSG-Fc" in the present disclosure.

In some embodiments, a fusion protein as disclosed herein may further comprise a linker sequence between the TWSG polypeptide and the Fc polypeptide. Such linker sequence may be of any length permitted or preferred for general fusion proteins or for the fusion protein of TWSG-Fc. For example, the linker sequence may comprise of a structure of X-(G)$_n$-Y, wherein X is absent or at least one amino acid residue, preferably T or S, wherein n is an integer having a value of at least 1, preferably 3 or 4; and wherein Y is absent or at least one amino acid residue, preferably S. In some embodiments, the linker sequence comprises TGGG (SEQ ID NO: 16), SGGG (SEQ ID NO: 17), TGGGG (SEQ ID NO: 18), SGGGG (SEQ ID NO: 19), GGGGS (SEQ ID NO: 20), GGGG (SEQ ID NO: 21), or GGG, preferably TGGG (SEQ ID NO: 16).

In certain aspects, the present disclosure provides a TWSG-Fc fusion protein comprising a polypeptide encodable by a polynucleotide comprising a nucleic acid sequence at least about 60, 65, 70, 75, 80, 85, 90, 91, 92, 93, 94, 95, 96, 97, 98, 99, or 100% identical to the sequence of SEQ ID NO: 14. In some embodiments, the polypeptide is encodable by a polynucleotide comprising a nucleic acid sequence at least 80% identical to the sequence of SEQ ID NO: 14. In some embodiments, the polypeptide is encodable by a polynucleotide comprising a nucleic acid sequence at least 85% identical to the sequence of SEQ ID NO: 14. In some embodiments, the polypeptide is encodable by a polynucleotide comprising a nucleic acid sequence at least 90% identical to the sequence of SEQ ID NO: 14. In some embodiments, the polypeptide is encodable by a polynucleotide comprising a nucleic acid sequence at least 95% identical to the sequence of SEQ ID NO: 14. In some embodiments, the polypeptide is encodable by a polynucleotide comprising a nucleic acid sequence at least 99% identical to the sequence of SEQ ID NO: 14. In some embodiments, the polypeptide is encodable by a polynucleotide comprising a nucleic acid sequence of SEQ ID NO: 14.

In some embodiments, the polypeptide is encodable by a polynucleotide that hybridizes, e.g., under highly stringent conditions to a nucleic acid sequence that is complementary to the sequence of SEQ ID NO: 14. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

The present disclosure further provides a TWSG-Fc fusion protein comprising a polypeptide comprising an amino acid sequence at least about 60, 65, 70, 75, 80, 85, 90, 91, 92, 93, 94, 95, 96, 97, 98, 99, or 100% identical to the sequence of SEQ ID NO: 9. In some embodiments, the polypeptide comprises an amino acid sequence at least 80% identical to the sequence of SEQ ID NO: 9. In some embodiments, the polypeptide comprises an amino acid sequence at least 85% identical to the sequence of SEQ ID NO: 9. In some embodiments, the polypeptide comprises an amino acid sequence at least 90% identical to the sequence of SEQ ID NO: 9. In some embodiments, the polypeptide comprises an amino acid sequence at least 95% identical to the sequence of SEQ ID NO: 9. In some embodiments, the polypeptide comprises an amino acid sequence at least 99% identical to the sequence of SEQ ID NO: 9. In some embodiments, the polypeptide comprises an amino acid sequence of SEQ ID NO: 9.

In some embodiments, the polypeptide provided in the present disclosure is encodable by a polynucleotide that hybridizes, e.g., under highly stringent conditions to a nucleic acid sequence that is complementary to the sequence of a polynucleotide encoding a polypeptide comprising an amino acid sequence of SEQ ID NO: 9. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

The present disclosure further provides a TWSG-Fc fusion protein comprising a polypeptide comprising an amino acid sequence at least about 60, 65, 70, 75, 80, 85, 90, 91, 92, 93, 94, 95, 96, 97, 98, 99, or 100% identical to the sequence of SEQ ID NO: 13. In some embodiments, the polypeptide comprises an amino acid sequence at least 80% identical to the sequence of SEQ ID NO: 13. In some embodiments, the polypeptide comprises an amino acid sequence at least 85% identical to the sequence of SEQ ID NO: 13. In some embodiments, the polypeptide comprises an amino acid sequence at least 90% identical to the sequence of SEQ ID NO: 13. In some embodiments, the polypeptide comprises an amino acid sequence at least 95% identical to the sequence of SEQ ID NO: 13. In some embodiments, the polypeptide comprises an amino acid sequence at least 99% identical to the sequence of SEQ ID NO: 13. In some embodiments, the polypeptide comprises an amino acid sequence of SEQ ID NO: 13.

In some embodiments, the polypeptide provided in the present disclosure is encodable by a polynucleotide that hybridizes, e.g., under highly stringent conditions to a nucleic acid sequence that is complementary to the sequence of a polynucleotide encoding a polypeptide comprising an amino acid sequence of SEQ ID NO: 13. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In some embodiments, the TWSG-Fc fusion protein or polypeptide of the present disclosure comprises wild-type or naturally occurring amino acid sequences for at least one of the TWSG portion and the Fc portion. In other embodiments, such polypeptide comprises at least one amino acid substitution relative to the wild-type or naturally occurring sequences. Such amino acid substitution may be, for example, in a potential glycosylation site in order to, for example, remove a potential glycosylation site. Such amino acid substitution may be, for example, in a site potentially affecting the biological function and/or interaction affinity of the Fc polypeptide. In some embodiments, such polypeptide comprises at least one amino acid substitution at at least one N-linked glycosylation site in SEQ ID NO: 9. In other embodiments, such polypeptide comprises at least one amino acid substitution at at least one N-linked glycosylation site in SEQ ID NO: 13.

In certain aspects, the present disclosure provides a TWSG-Fc fusion protein or polypeptide capable of binding to, preferably inhibiting, at least one bone morphogenetic proteins (BMP), such as a BMP selected from BMP2, BMP4, BMP6, BMP7, and BMP9. In some embodiments, the TWSG-Fc fusion protein or polypeptide is capable of binding to, preferably inhibiting, at least one bone morphogenetic proteins (BMP) with a $K_D$ less than 4.5 nM (or preferably, no more than 4.4 nM). In some embodiments, the TWSG-Fc fusion protein or polypeptide is capable of binding to, preferably inhibiting, at least one bone morphogenetic proteins (BMP) in a sub-nanomolar affinity. For example, the TWSG-Fc fusion protein or polypeptide may be capable of binding to at least one of BMPs with a $K_D$ no more than 1 nM, 0.5 nM, 0.33 nM, or less. In some embodiments, the TWSG-Fc fusion protein or polypeptide is capable of binding with a $K_D$ no more than 1 nM, 0.5 nM, or 0.33 nM (or preferably, no more than 0.33, 0.30, or 0.23 nM) to at least one BMP selected from BMP2, BMP4, BMP6, and BMP7. In some embodiments, the TWSG-Fc fusion protein or polypeptide is capable of binding with a $K_D$ no more than 1 nM, 0.5 nM, or 0.33 nM (or preferably, no more than 0.33, 0.30, or 0.23 nM) to at least two BMPs selected from BMP2, BMP4, BMP6, and BMP7. In some embodiments, the TWSG-Fc fusion protein or polypeptide is capable of binding with a $K_D$ no more than 1 nM, 0.5 nM, or 0.33 nM (or preferably, no more than 0.33, 0.30, or 0.23 nM) to at least three BMPs selected from BMP2, BMP4, BMP6, and BMP7. In some embodiments, the TWSG-Fc fusion protein or polypeptide is capable of binding with a $K_D$ no more than 1 nM, 0.5 nM, or 0.33 nM (or preferably, no more than 0.33, 0.30, or 0.23 nM) to BMP2, BMP4, BMP6, and BMP7. Such binding between the TWSG-Fc fusion protein or polypeptide and the BMPs may be detected and/or measured with any suitable technology, such as an in vitro binding assay detected by surface plasmon resonance.

In some embodiments, the TWSG-Fc fusion protein or polypeptide is capable of inhibiting at least one of bone morphogenetic proteins (BMPs), such as BMP2, BMP4, BMP6, and BMP7. For example, the TWSG-Fc fusion protein or polypeptide may be capable of inhibiting at least one of BMPs with an $IC_{50}$ less than 31 nM.

In some embodiments, the TWSG-Fc fusion protein or polypeptide is capable of inhibiting at least one of bone morphogenetic proteins (BMPs) with an $IC_{50}$ at nanomolar level. For example, the TWSG-Fc fusion protein or polypeptide may be capable of inhibiting at least one of BMPs with an $IC_{50}$ no more than 5 nM, 4 nM, 3.7 nM, or 3 nM (or preferably, no more than 3.7, 2.2, or 1.5 nM). In some embodiments, the TWSG-Fc fusion protein or polypeptide is capable of inhibiting at least one of BMPs selected from BMP4, BMP6, and BMP7 at an $IC_{50}$ no more than 5 nM or 3.7 nM (or preferably, no more than 3.7, 2.2, or 1.5 nM). In some embodiments, the TWSG-Fc fusion protein or polypeptide is capable of inhibiting at least two BMPs selected from BMP4, BMP6, and BMP7 at an $IC_{50}$ no more than 5 nM or 3.7 nM (or preferably, no more than 3.7, 2.2, or 1.5 nM). In some embodiments, the TWSG-Fc fusion protein or polypeptide is capable of inhibiting BMP4, BMP6, and BMP7 at an $IC_{50}$ no more than 5 nM or 3.7 nM (or preferably, no more than 3.7, 2.2, or 1.5 nM). Such inhibition includes inhibition of at least one aspect of BMP activity, such as BMP-mediated cell signaling processes. Such BMP-mediated cell signaling processes may be mediated by at least one of BMP substrates and/or downstream signaling messengers of BMPs, including, at least, Smad proteins (e.g., Smad 1, Smad 5, etc.). In some embodiments, the TWSG-Fc fusion protein or polypeptide is capable of inhibiting at least one aspect of BMP-mediated cell signaling processes through at least one of Smad1 and Smad 5. Such inhibition may be detected and/or measured with any suitable technology, such as by a cell-based assay, e.g., an in vitro cell-based assay. Such cell-based assay may utilize at least one BMP response element in, e.g., a pGL3 BRE reporter plasmid.

In certain aspects, the present disclosure provides a multimeric polypeptide complex comprising the TWSG-Fc fusion protein or polypeptide described herein. Such complex may comprise the TWSG-Fc fusion protein or polypeptide and at least one another homologous or heterologous polypeptide or at least one another molecule of the same TWSG-Fc fusion protein or polypeptide. Such multimeric polypeptide complex may be, for example, a dimer, trimer, or an oligomer containing at least 4, 5, 6, 7, 8, 9, 10, or more monomer polypeptides. In the multimeric polypeptide complex, at least two (e.g., 2, 3, 4, 5, 6, 7, 8, 9, 10, or more) of the monomer polypeptides may have the same amino acid sequence (e.g., the TWSG-Fc fusion protein or polypeptide described herein) or have a high sequence homology (e.g., of at least about 60, 65, 70, 75, 80, 85, 90, 91, 92, 93, 94, 95, 96, 97, 98, 99, or 100% identity). In some embodiments, the multimeric polypeptide complex is a homodimer (e.g., comprising two molecules of the TWSG-Fc fusion protein or polypeptide). In other embodiments, the multimeric polypeptide complex is a heterodimer (e.g., comprising TWSG-Fc fusion protein or polypeptide and another heterologous protein or polypeptide). The monomer polypeptides in the multimeric polypeptide complex may contact each other through at least one covalent bond or noncovalent interaction known in the art. For example, linkers may be added to such monomer polypeptides to facilitate interaction to form the multimeric polypeptide complex. In another nonlimiting example, the Fc portion of the TWSG-Fc fusion protein or polypeptide may be used to interact with at least one another monomer polypeptide. In some embodiments, two TWSG-Fc fusion proteins or polypeptides (with a same Fc portion or different Fc portions comprising different mutations, substitutions, chemical modifications, etc.) form a dimer. Such dimer may be either a homodimer (in case using two molecules of a same TWSG-Fc fusion protein or polypeptide) or a heterodimer (in case using different fusion protein or polypeptides comprising different sequences in their TWSG portions and/or Fc portions). In other embodiments, multiple TWSG-Fc fusion proteins or polypeptides (as homo-monomers or hetero-monomers) form a multimeric polypeptide complex.

In certain aspects, the present disclosure provides a composition or formulation comprising the TWSG-Fc fusion protein or polypeptide described herein and a pharmaceutically acceptable carrier. In some embodiments, such composition or formulation is a pharmaceutical composition or formulation.

In certain aspects, the present disclosure provides a composition or formulation comprising the multimeric polypeptide complex comprising the TWSG-Fc fusion protein or polypeptide described herein and a pharmaceutically acceptable carrier. In some embodiments, such composition or formulation is a pharmaceutical composition or formulation.

In other aspects, the present disclosure provides novel Twisted gastrulation (TWSG) polynucleotides, such as an isolated TWSG polynucleotide or an at least partly purified TWSG polynucleotide. In some embodiments, the present disclosure provides an isolated and at least partly purified TWSG polynucleotide. For example, the present disclosure provides a polynucleotide encoding a TWSG-Fc fusion protein or polypeptide as described herein. Such polynucleotide may comprise a DNA, an RNA, or an mRNA molecule.

In certain embodiments, the TWSG portion of the polynucleotide comprises a nucleic acid sequence at least about 60, 65, 70, 75, 80, 85, 90, 91, 92, 93, 94, 95, 96, 97, 98, 99, or 100% identical to the sequence of SEQ ID NO: 2. In some embodiments, the TWSG portion of the polynucleotide comprises a nucleic acid sequence at least 80% identical to the sequence of SEQ ID NO: 2. In some embodiments, the TWSG portion of the polynucleotide comprises a nucleic acid sequence at least 85% identical to the sequence of SEQ ID NO: 2. In some embodiments, the TWSG portion of the polynucleotide comprises a nucleic acid sequence at least 90% identical to the sequence of SEQ ID NO: 2. In some embodiments, the TWSG portion of the polynucleotide comprises a nucleic acid sequence at least 95% identical to the sequence of SEQ ID NO: 2. In some embodiments, the TWSG portion of the polynucleotide comprises a nucleic acid sequence at least 99% identical to the sequence of SEQ ID NO: 2. In some embodiments, the TWSG portion of the polynucleotide comprises a nucleic acid sequence of SEQ ID NO: 2. In some embodiments, the TWSG portion of the polynucleotide hybridizes, e.g., under highly stringent conditions to a nucleic acid sequence that is complementary to the sequence of SEQ ID NO: 2. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In some embodiments, the TWSG portion of the polynucleotide encodes a TWSG polypeptide comprising an amino acid sequence at least about 60, 65, 70, 75, 80, 85, 90, 91, 92, 93, 94, 95, 96, 97, 98, 99, or 100% identical to the sequence of SEQ ID NO: 8. In some embodiments, the encoded TWSG polypeptide comprises an amino acid sequence at least 80% identical to the sequence of SEQ ID NO: 8. In some embodiments, the encoded TWSG polypeptide comprises an amino acid sequence at least 85% identical to the sequence of SEQ ID NO: 8. In some embodiments, the encoded TWSG polypeptide comprises an amino acid sequence at least 90% identical to the sequence of SEQ ID NO: 8. In some embodiments, the encoded TWSG polypeptide comprises an amino acid sequence at least 95% identical to the sequence of SEQ ID NO: 8. In some embodiments, the encoded TWSG polypeptide comprises an amino acid sequence at least 99% identical to the sequence of SEQ ID NO: 8. In some embodiments, the encoded TWSG polypeptide comprises an amino acid sequence of SEQ ID NO: 8.

In some embodiments, the TWSG portion of the polynucleotide comprises a wild-type or naturally occurring nucleic acid sequence. In other embodiments, the TWSG portion comprises at least one nucleic acid substitution relative to a wild-type or naturally occurring nucleic acid sequence. Such nucleic acid substitution may encode, for example, at least one amino acid substitution in the TWSG polypeptide, such as a potential glycosylation site in order to, for example, remove a potential glycosylation site. Alternatively, such nucleic acid substitution may encode at least one amino acid substitution in the encoded TWSG polypeptide at a site potentially affecting the biological function and/or interaction affinity of the encoded TWSG polypeptide.

In some embodiments, the TWSG polypeptide encoded by the polynucleotide described herein comprises a signal sequence, e.g., at the N-terminus of the encoded TWSG polypeptide. In other embodiments, the encoded TWSG polypeptide does not comprise a signal sequence.

In some embodiments, the Fc portion of the polynucleotide described herein hybridizes, e.g., under highly stringent conditions, to a nucleic acid sequence that is complementary to the sequence of a polynucleotide encoding a polypeptide comprising an amino acid sequence of SEQ ID NO: 3, 4, 5, 6, or 7. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In some embodiments, the polynucleotide provided in the present disclosure hybridizes, e.g., under highly stringent conditions, to a nucleic acid sequence that is complementary to the sequence of SEQ ID NO: 14. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In some embodiments, the polynucleotide provided in the present disclosure hybridizes, e.g., under highly stringent conditions to a nucleic acid sequence that is complementary to the sequence of a polynucleotide encoding a polypeptide comprising an amino acid sequence of SEQ ID NO: 9. In other embodiments, the polynucleotide provided in the present disclosure hybridizes, e.g., under highly stringent conditions to a nucleic acid sequence that is complementary to the sequence of a polynucleotide encoding a polypeptide comprising an amino acid sequence of SEQ ID NO: 13. Such highly stringent conditions may comprise hybridization in 6× sodium chloride/sodium citrate (SSC) at about 45° C. to about 65° C., followed by at least one wash in about 0.2×SSC to about 2.0×SSC at about 50° C. to about 65° C. In some embodiments, such highly stringent conditions may comprise hybridization in 6× sodium chloride/sodium citrate (SSC) at about 65° C., followed by a wash in 0.2×SSC at about 65° C.

In some embodiments, the polynucleotide of the present disclosure comprises wild-type or naturally occurring nucleic acid sequences for at least one of the TWSG portion and the Fc portion. In some embodiments, the polynucleotide comprises at least one nucleic acid substitution relative to wild-type or naturally occurring nucleic acid sequences. Such nucleic acid substitution may encode, for example, at least one amino acid substitution in the encoded TWSG-Fc fusion polypeptide. For example, the nucleic acid substitution may encode at least one amino acid substation in at least one potential glycosylation site in order to, for example, remove a potential glycosylation a potential glycosylation site. Alternatively, such nucleic acid substitution may encode at least one amino acid substitution in the encodable TWSG or Fc portion at at least one site potentially affecting the biological function and/or interaction affinity of such portion. In some embodiments, such polynucleotide comprises at least one nucleic acid substitution to SEQ ID NO: 14.

In certain aspects, the present disclosure provides a composition or formulation comprising a polynucleotide as described herein and a pharmaceutically acceptable carrier. In some embodiments, such composition or formulation is a pharmaceutical composition or formulation.

In certain aspects, the present disclosure provides a vector comprising at least one regulatory sequence operably linked to the polynucleotide encoding a TWSG-Fc fusion protein or polypeptide as described herein. In some embodiments, the vector is an expression vector (e.g., a plasmid) or a viral vector (e.g., an adenoviral (AV) vector or an advanced adenoviral (AAV) vector). In some embodiments, the expressed TWSG-Fc fusion protein or polypeptide forms a multimeric polypeptide complex described herein.

In certain aspects, the present disclosure provides a host cell comprising, preferably expressing a vector described herein. In some embodiments, the polynucleotide encoding a TWSG-Fc fusion protein or polypeptide described herein is produced in the host cell by expressing the vector. In some embodiments, the TWSG-Fc fusion protein or polypeptide produced in such host cell forms a multimeric polypeptide complex described herein. Such host cell may be any suitable cell, such as a eukaryotic cell or a bacterial cell. In some embodiments, the host cell is a mammalian cell, a vertebrate cell, a yeast cell, or an insect cell. In some embodiments, the host cell is a Chinese hamster ovary (CHO) cell.

In certain aspects, the present disclosure provides a kit or article comprising at least one of the TWSG-Fc fusion protein or polypeptide, the polynucleotide encoding such TWSG-Fc fusion protein or polypeptide, the composition, the vector, and the host cell described herein. Optionally, the kit or article may also comprise an administration device (e.g., an infusion device, an injection device, an inhale device, a nebulizer device, an implantable device, etc.) to administer such fusion protein or polypeptide, polynucleotide, composition, vector, and/or host cell to a subject (e.g., a mammal, such as a human). Optionally, the kit or article may also contain instructions for such administration. In some embodiments, the administered TWSG-Fc fusion protein or polypeptide produced forms a multimeric polypeptide complex described herein.

In certain aspects, the present disclosure provides a non-human animal engineered to express, or to overexpress, the TWSG-Fc fusion protein or polypeptide, and/or the polynucleotide encoding the TWSG-Fc fusion protein or polypeptide, as described herein. In some embodiments, such non-human animal is genetically engineered. In some embodiments, the expressed or overexpressed TWSG-Fc fusion protein or polypeptide forms a multimeric polypeptide complex described herein in such non-human animal.

In certain aspects, the present disclosure provides a method of producing a TWSG-Fc fusion protein or polypeptide, comprising:
  i) providing a cell comprising a polynucleotide encoding the TWSG-Fc fusion protein or polypeptide, as described herein; and
  ii) culturing the cell under conditions suitable for expression of the TWSG-Fc fusion polypeptide encoded by the polynucleotide, and optionally
  iii) recovering the expressed TWSG-Fc fusion polypeptide.

In some embodiments, the TWSG-Fc fusion protein or polypeptide produced through such method forms a multimeric polypeptide complex described herein.

Any suitable methods of protein production in cell culture may be used herein. In some embodiments, the cell for producing TWSG-Fc is a mammalian cell, such as a CHO cell.

In certain aspects, the present disclosure provides a method of inhibiting BMP signaling in a cell, tissue, or organ, comprising contacting the cell, tissue, or organ with a TWSG-Fc fusion protein or polypeptide, multimeric polypeptide complex, polynucleotide, composition, vector, and/or host cell, as described herein.

In certain aspects, the present disclosure provides a method of increasing red blood cell and/or hemoglobin levels, or reducing blood transfusion-dependence (TD), in a subject, comprising administering to the subject a TWSG-Fc fusion protein or polypeptide, multimeric polypeptide complex, polynucleotide, composition, vector, and/or host cell, as described herein.

In certain aspects, the present disclosure provides a method of increasing iron levels in a subject, comprising administering to the subject a TWSG-Fc fusion protein or polypeptide, multimeric polypeptide complex, polynucleotide, composition, vector, and/or host cell, as described herein. In some embodiments, the increase of iron level in the subject occurs in the spleen. In some embodiments, the increase of iron level in the subject occurs in spleen but no other tissues.

In certain aspects, the present disclosure provides a method of treating iron overload in a subject, comprising administering to the subject a TWSG-Fc fusion protein or polypeptide, multimeric polypeptide complex, polynucleotide, composition, vector, and/or host cell, as described herein.

In certain aspects, the present disclosure provides a method of preventing iron overload in a subject, comprising administering to the subject a TWSG-Fc fusion protein or polypeptide, multimeric polypeptide complex, polynucleotide, composition, vector, and/or host cell, as described herein.

In certain aspects, the present disclosure provides a method of treating dysregulation of BMP signaling in a subject, comprising administering to the subject a TWSG-Fc fusion protein or polypeptide, multimeric polypeptide complex, polynucleotide, composition, vector, and/or host cell, as described herein. In some embodiments, the dysregulation of BMP signaling results in at least one of anemia, splenomegaly, erythroblast-induced bone pathology, iron overload, and thalassemia syndromes in the subject. In some embodiments, the dysregulation of BMP signaling results in ineffective erythropoiesis in the subject. In some embodiments, treating the dysregulation of BMP signaling results in treating ineffective erythropoiesis in the subject. In some embodiments, treating the dysregulation of BMP signaling results in treating at least one of anemia, splenomegaly, erythroblast-induced bone pathology, iron overload, and thalassemia syndromes.

In certain aspects, the present disclosure provides a method of treating anemia in a subject, comprising administering to the subject a TWSG-Fc fusion protein or polypeptide, multimeric polypeptide complex, polynucleotide, composition, vector, and/or host cell, as described herein.

In certain aspects, the present disclosure provides a method of treating anemia in a subject, comprising administering to the subject a fusion protein comprising a Twisted Gastrulation (TWSG) polypeptide and a fragment crystallizable region (Fc) polypeptide, or a multimeric polypeptide complex comprising such fusion protein. In some embodiments, such fusion protein comprises the sequence of SEQ ID NO: 9. In other embodiments, such fusion protein comprises the sequence of SEQ ID NO: 13.

In certain aspects, the present disclosure provides a method of treating anemia in a subject, comprising administering to the subject a polynucleotide encoding a fusion protein comprising a Twisted Gastrulation (TWSG) polypeptide and a fragment crystallizable region (Fc) polypeptide. For example, such polynucleotide may comprise the sequence of SEQ ID NO: 14. In some embodiments, such fusion protein comprises the sequence of SEQ ID NO: 9. In other embodiments, such fusion protein comprises the sequence of SEQ ID NO: 13. In a non-limiting example, such fusion protein forms a multimeric polypeptide complex described herein in the subject.

In some embodiments, the anemia described herein comprises inherited anemia, acquired anemia, anemia of chronic disease or inflammation, dyserythropoietic anemia (Types I and II), sickle cell anemia, hereditary spherocytosis, pyruvate kinase deficiency-related anemia, or megaloblastic anemia. The anemia may be any anemia-related disease or disorder described in the present disclosure.

Any suitable method may be used for administration in the therapeutic methods described herein. For example, the administration may be through at least one of topical, enteral, and parenteral routes. In some embodiments, the administration is through at least one of oral and nasal routes. In other embodiments, the administration is through at least one of intravenous, subcutaneous, intraarterial, intraperitoneal, and intramuscular routes.

In certain aspects, the present disclosure provides a therapeutic method, as described herein, further comprising conjointly administering a second pharmaceutical agent or second therapeutic practice. Such second pharmaceutical agent may be, for example, EPO or an agonist or analog thereof, or another BMP antagonist. Such second therapeutic practice may be, for example, blood transfusion.

In certain aspects, the present disclosure provides a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, for inhibiting BMP signaling, increasing red blood cell and/or hemoglobin levels, reducing blood transfusion-dependence (TD), increasing iron levels, treating or preventing iron overload, or treating dysregulation of BMP signaling in a subject.

In one aspect, the present disclosure provides a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, for treating anemia in a subject.

In certain aspects, the present disclosure provides a use of a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, for inhibiting BMP signaling, increasing red blood cell and/or hemoglobin levels, reducing blood transfusion-dependence (TD), increasing iron levels, treating or preventing iron overload, or treating dysregulation of BMP signaling in a subject.

In one aspect, the present disclosure provides a use of a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, for treating anemia in a subject.

In certain aspects, the present disclosure provides a use of a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, the manufacture of a medicament for the treatment of inhibiting BMP signaling, increasing red blood cell and/or hemoglobin levels, reducing blood transfusion-dependence (TD), increasing iron levels, treating or preventing iron overload, or treating dysregulation of BMP signaling in a subject.

In one aspect, the present disclosure provides a use of a TWSG-Fc fusion protein or polypeptide, a multimeric polypeptide complex comprising such fusion protein or polypeptide, a polynucleotide encoding such fusion protein or polypeptide, a composition comprising such fusion protein or polypeptide or such polynucleotide, a vector comprising such polynucleotide, and/or a host cell expressing such vector, as described herein, for the manufacture of a medicament for the treatment of anemia in a subject.

The subject of the various methods and uses described herein is preferably a mammal, most preferably a human.

BRIEF DESCRIPTION OF THE DRAWINGS

FIG. 1 depicts the amino acid sequence of processed human TWSG (SEQ ID NO: 8). Dotted underline denotes potential N-glycosylation sites.

FIG. 2 depicts the amino acid sequence of processed human TWSG-Fc (SEQ ID NO: 9). Solid underline indicates the linker between the TWSG portion and the Fc portion.

FIG. 3 depicts the amino acid sequence of unprocessed human TWSG-Fc (SEQ ID NO: 13). Solid underlines indicate the signal sequence in the N-terminus of TWSG-Fc and the linker between the TWSG portion and the Fc portion.

FIG. 4 depicts a nucleotide sequence encoding unprocessed human TWSG-Fc (SEQ ID NO: 14).

FIG. 7 shows effects of human TWSG-Fc (labeled as "TWSG-G1Fc") vs. vehicle control on RBC count (FIG. 7A) and hemoglobin concentration (FIG. 7B) in mice. Compared to vehicle, treatment of wild-type mice with TWSG-Fc for 4 weeks increased RBC count by 15% (A) and hemoglobin concentration by 12% (B). Data are means±SEM; n=5 per group;  $P<0.01$, * $P<0.001$.

DETAILED DESCRIPTION OF THE INVENTION

1. Overview

Figure 5:
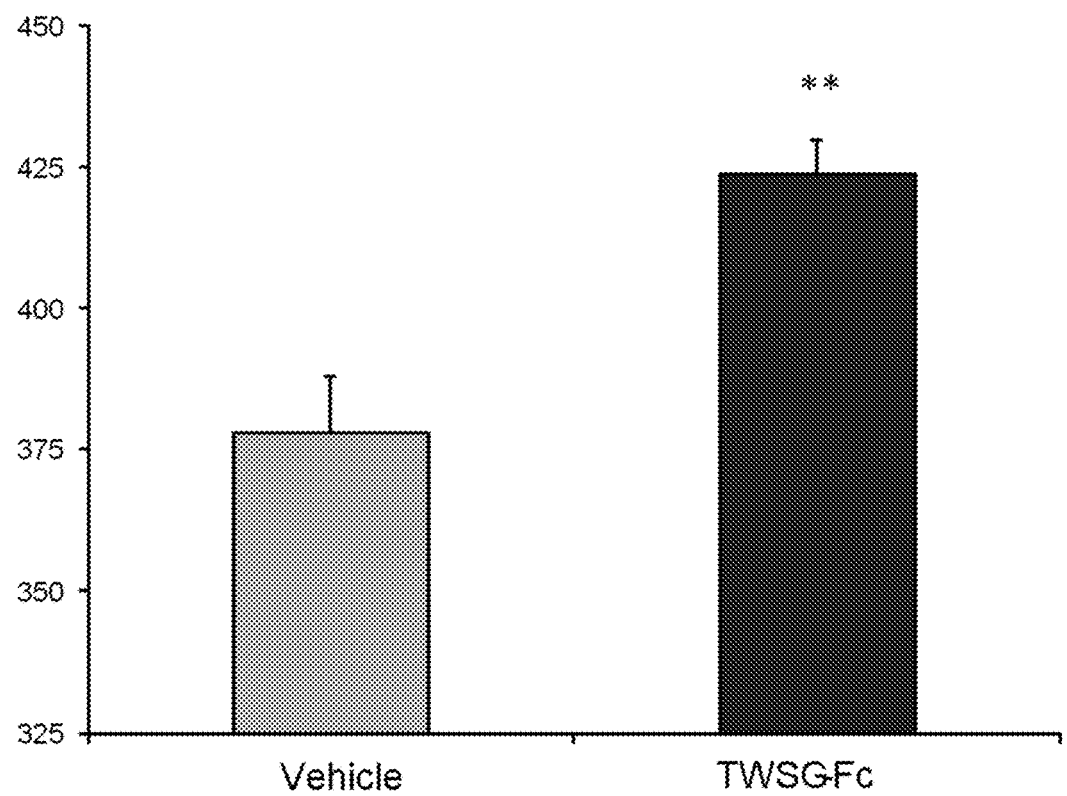
FIG. 5 shows the effect of human TWSG-Fc vs. vehicle control on circulating iron concentrations in mice. Compared to vehicle, treatment of wild-type mice with TWSG-Fc for 1 week increased serum iron by 12%. Data are means±SEM; n=5 per group; ** $P<0.01$.

In part, the present disclosure provides novel TWSG polypeptides to promote iron availability and increased levels of red blood cells and/or hemoglobin in animals. TWSG is a secreted protein that regulates signaling by certain bone morphogenetic proteins (BMPs), which are a prominent group of ligands in the superfamily that also includes transforming growth factor-β (TGF-β), growth differentiation factors (GDFs), and activins/inhibins. This superfamily contains a variety of growth factors that share common sequence elements and structural motifs. These proteins are known to exert biological effects on a large variety of cell types during embryogenesis as well as postnatally in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-β family, it is often possible to cause significant physiological changes in an organism. For example, the Piedmontese and Belgian Blue cattle breeds carry a loss-of-function mutation in the gene encoding myostatin (MSTN; also called GDF8) that causes a marked increase in muscle mass. Grobet et al., Nat Genet. 1997, 17(1): 71-4. Furthermore, in humans, inactive alleles of MSTN are associated with increased muscle mass and, reportedly, exceptional strength. Schuelke et al., N Engl J Med 2004, 350:2682-8.

TGF-β superfamily signaling is mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Ligand binding triggers formation of a heteromeric complex of type I and type II receptors, phosphorylation of type I receptor by type II receptor, and subsequent activation of Smad1/5/8 or Smad2/3 transcription factors, which then act in the nucleus to regulate gene expression.

Twisted gastrulation (abbreviated TWSG or TWSG1 in mammals and Tsg in nonmammals; collectively as "TWSG" in the instant disclosure) is a highly conserved, secreted protein implicated as an important regulator of BMP signaling during embryogenesis, particularly based on studies in the fruit fly (*Drosophila*) and frog (*Xenopus*) (Mason et al., 1994, Genes Dev 8:1489-1501; Graf et al., 2001, Mamm Genome 12:554-560; Zakin et al., 2010, Curr Biol 20:R89-92). TWSG is often classified in a diverse group of extracellular proteins having the shared ability to antagonize BMP signaling (Avsian-Kretchmer et al., 2004, Mol Endocrinol 18:1-12; Gazzerro et al., 2006, Rev Endocr Metab Disord 7:51-65; Walsh et al., 2010, Trends Cell Biol 20:244-256). However, embryogenic studies indicate that TWSG/Tsg can either promote (Oelgeschläger et al., 2000, Nature 405:757-763; Little et al., 2004, Development 131:5825-5835; Xie et al., 2004, Development 132:383-391) or inhibit (Scott et al., 2001, Nature 410:475-478; Ross et al., 2001, Nature 410:479-483; Chang et al., 2001, Nature 410:483-487) BMP signaling in a context-dependent manner involving direct BMP binding as well as interaction with other proteins such as chordin (Larrain et al., 2001, Development 128:4439-4447). When chordin levels are low, the binary complex of TWSG/Tsg with BMP is thought to be permissive for BMP signaling by maintaining ligand solubility (De Robertis et al., 2000, Nat Rev Genet 1:171-181; Zakin et al., 2010, Curr Biol 20:R89-92; Rider et al., 2010, Biochem J 429:1-12). To date, the specific ligands shown to bind TWSG/Tsg are BMP2, BMP4, and BMP7 (Oelgeschläger et al., 2000, Nature 405:757-763; Chang et al., 2001, Nature 410:483-487; Zakin et al., 2005, Development 132:2489-2499).

Like other ligands in the TGFβ superfamily, BMPs contain a characteristic cysteine knot motif and are secreted as precursor molecules containing a larger N-terminal prodomain that is removed by proteolytic cleavage to generate mature dimeric ligand (Harrison et al., Growth Factors 29:174, 2011; Shi et al., Nature 474:343, 2011). Although initially named for their generally shared ability to induce bone formation (Cheng et al., 2003, J Bone Joint Surg Am 85-A:1544-1552), BMPs are now recognized to play critical roles in early embryogenesis and to exhibit a broad spectrum of biological activities in later stages of development (Hogan et al., 1996, Genes Dev 10:1580-1594; Gazzerro et al., 2006, Rev Endocr Metab Disord 7:51-65).

Gene knockout studies in mice have been important in identifying developmental and/or physiologic roles of individual BMPs in mammals for which other BMPs cannot effectively substitute (Chang et al., 2002, Endocr Rev 23:787-823). BMP2 and BMP4 are closely related, and global loss of function of either gene causes early embryonic lethality in mice (Winnier et al., 1995, Genes Dev 9:2105-2116; Zhang et al., 1996, Development 122:2977-2986). Studies with BMP2/BMP4 compound mutant mice have revealed functions of BMP2 in development of multiple organ systems, including the skeleton, heart, eye, ventral body wall, and placenta (Goldman et al., 2009, Mech Develop 126:117-127). Whereas BMP2, BMP4, BMP7, and the closely related BMP6 can all stimulate bone formation (Cheng et al., 2003, J Bone Joint Surg Am 85-A:1544-1552), conditional ablation of these individual genes produces markedly different outcomes. Combined conditional knockout of BMP2 and BMP4 in embryonic limb buds causes severe impairment of osteogenesis (Bandyopadhyay et al., 2006, PLOS Genet 2:e216). Conditional knockout of BMP2 in limb bones leads to spontaneous fractures in mice and reveals an obligatory role for BMP2 in fracture healing (Tsuji et al., 2006, Nat Genet 38:1424-1429), whereas conditional knockout of BMP7 has no effect on postnatal limb growth or maintenance of bone mass, thus indicating that other factors present in adult bone can compensate for its absence (Tsuji et al., 2010, J Orthop Res 28:384-389). Endogenous TWSG has been implicated as a negative regulator of pro-osteoclastic BMP2 signaling in mice (Pham et al., 2011, J Cell Biochem 112:793-803). BMP2, but not BMP4, also serves a critical role in cartilage formation during bone development (Shu et al., 2011, J Cell Sci 124:3428-3440). Finally, BMP6 ablation in mice does not cause major skeletal defects (Solloway et al., 1998, Dev Genet 22:321-339) but does alter bone morphometry consistent with a non-redundant role for BMP6 in periosteal bone formation (Perry et al., 2008, Bone 42:216-225).

Significantly, BMP4 and BMP6 are implicated in postnatal erythropoiesis and/or iron homeostasis. The body has evolved sophisticated mechanisms for regulating iron levels because dietary iron is undependable and low plasma iron levels limit iron uptake and hemoglobin synthesis by erythroid precursors, causing anemia. On the other hand, excessive accumulation of iron (iron overload) causes damage to cells and tissues due in part to generation of reactive oxygen species (Fibach et al., 2008, Curr Mol Med 8:609-619). The hepatic peptide hormone hepcidin is now widely considered to be the master regulator of iron homeostasis due to its ability to promote degradation of the iron-transport protein ferroportin which is otherwise present on the surface of iron-absorbing enterocytes, iron-recycling macrophages, and iron-storing hepatocytes (Ganz et al., 2012, Biochim Biophys Acta 1823:1434-1443). In mice, BMP6 and its co-receptor hemojuvelin [encoded by the hemochromatosis type 2 gene (HFE2) and also known as repulsive guidance molecule C (RGMc)] are essential for normal iron homeostasis since their loss interferes with the hepcidin response to iron loading (Niederkofler et al., 2005, J Clin Invest 115: 2180-2186; Babitt et al., 2006, Nat Genet 38:531-539; Camaschella, 2009, Nat Genet 41:386-388; Meynard et al., 2009, Nat Genet 41:478-481; Andriopoulos et al., 2009, Nat Genet 41:482-487). Other BMPs, including BMP2, BMP4, BMP7, and BMP9, are able to stimulate hepcidin expression in vitro (Xia et al., 2008, Blood 111:5195-5204), but their physiologic relevance has not been established (Ganz et al., 2012, Biochim Biophys Acta 1823: 1434-1443).

In addition to BMP6 involvement in iron homeostasis, BMP4 has been implicated as an important ligand in a stress-erythropoiesis pathway in mice, which mediates induction of compensatory erythropoiesis in response to acute and chronic anemia (Paulson et al., 2011, Curr Opin Hematol 18:139-145). This stress-erythropoiesis pathway is distinct from steady-state erythropoiesis and occurs in mice in the fetal liver, adult liver, and adult spleen. In this pathway, BMP4 is thought to promote the expansion of a population of specialized stress-erythroid progenitors in response to an acute anemia stimulus, and therefore inhibition of BMP4 signaling by itself would be predicted to block the stress-erythropoiesis response and be counterproductive in treating anemia.

Specific BMPs shown to bind to TWSG are restricted in which combinations of receptor heterodimers they use. BMP2 and BMP4 signal through the type I receptors activin receptor-like kinase-3 (ALK3 or BMPRIA) and ALK6 (BMPRIB), and through the type II receptors BMP receptor type II (BMPRII), activin receptor type IIA (ActRIIA or ACVR2A), and activin receptor type IIB (ActRIIB or ACVR2B) (Mueller et al., 2012 FEBS Lett 586:1846-1859). In addition to heteromeric complexes containing these receptors, BMP6 and BMP7 can signal through combinations containing ALK2 (ActRIA or ACVR1) as well. Upon ligand-induced formation of heteromeric receptor complex, ALK2, ALK3, and ALK6 typically activate the Smad1/5/8 subfamily of intracellular effectors to regulate gene expression (Miyazono et al., 2010, J Biochem 147:35-51).

As demonstrated herein, a TWSG polypeptide selectively inhibits signaling by certain BMPs, unexpectedly increases red blood cell levels in mice in vivo, and exerts beneficial effects on systemic iron availability in vivo that support its promotion of red blood cell formation. Effects of TWSG polypeptides may be particularly useful in treating anemia of inflammation (also known as anemia of chronic disease), which results when inflammatory processes increase hepcidin expression and thereby limit iron availability for erythropoiesis. It should be noted that erythropoiesis is a complex process, regulated by a variety of factors, including EPO, G-CSF, and iron homeostasis. The terms "increase red blood cell levels" and "promote red blood cell formation" refer to clinically observable metrics, such as hematocrit, red blood cell counts and hemoglobin measurements, and are intended to be neutral as to the mechanism by which such changes occur.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. TWSG Polypeptides

In certain aspects, the invention relates to TWSG polypeptides, e.g., soluble TWSG polypeptides, comprising, for example, fragments, functional variants, and modified forms of wild-type TWSG polypeptides. In certain embodiments, the TWSG polypeptides have the same or at least one similar biological activity as a corresponding wild-type TWSG polypeptide. For example, a TWSG polypeptide of the invention may bind to and inhibit the function of a BMP ligand (e.g., BMP2, BMP4, BMP6, BMP7, or BMP9). Optionally, a TWSG polypeptide increases iron availability, red blood numbers, and/or circulating hemoglobin concentrations. Examples of TWSG polypeptides include human TWSG precursor polypeptides (SEQ ID NO: 1) having one or more sequence variations, and soluble human TWSG polypeptides (e.g., SEQ ID NOs: 8, 9, and 13) having one or more sequence variations.

As used herein, the term "TWSG" refers to twisted gastrulation proteins from any species and variants derived from such TWSG proteins by mutagenesis or other modification. Reference to TWSG herein is understood to be a reference to any one of the currently identified forms. Members of the TWSG family are secreted proteins composed of an N-terminal domain that is essential for BMP binding and a C-terminal domain that interacts with chordin and other proteins. The amino acid sequence of mature native human TWSG (SEQ ID NO: 8) is illustrated in FIG. 1.

The term "TWSG polypeptide" includes polypeptides comprising any naturally occurring polypeptide of a TWSG family member as well as any variants thereof (including mutants, fragments, fusions, and peptidomimetic forms) that retain a useful activity. For example, TWSG polypeptides include polypeptides derived from the sequence of any known TWSG having a sequence at least about 80% identical to the sequence of an TWSG polypeptide, and optionally at least 85%, 90%, 91%, 92%, 93%, 94%, 95%, 96%, 97%, 98%, 99% or 100% identity. For example, a TWSG polypeptide may bind to and inhibit the function of a BMP and/or other ligand in the TGFβ superfamily. A TWSG polypeptide may be selected for activity in promoting red blood cell formation in vivo. Examples of TWSG polypeptides include human TWSG precursor polypeptide (SEQ ID NO: 1) and soluble human TWSG polypeptides (e.g., SEQ ID NOs: 8, 9, and 13). Numbering of amino acids for all TWSG polypeptides described herein is based on the numbering for SEQ ID NO: 1, unless specifically designated otherwise.

The human TWSG precursor sequence (NCBI Reference Sequence NP_065699.1) is as follows:

```
                                                              (SEQ ID NO: 1)
  1 MKLHYVAVLT LAILMFLTWL PESLSCNKAL CASDVSKCLI QELCQCRPGE

51 GNCSCCKECM LCLGALWDEC CDCVGMCNPR NYSDTPPTSK STVEELHEPI

101 PSLFRALTEG DTQLNWNIVS FPVAEELSHH ENLVSFLETV NQPHHQNVSV

151 PSNNVHAPYS SDKEHMCTVV YFDDCMSIHQ CKISCESMGA SKYRWFHNAC

201 CECIGPECID YGSKTVKCMN CMF
```

The leader (signal) sequence and three potential N-linked glycosylation sites are underlined.

A nucleotide sequence encoding human TWSG precursor (nucleotides 192-860 of NCBI Reference Sequence NM_020648.5) is as follows:

```
                                                              (SEQ ID NO: 2)
  1 ATGAAGTTAC ACTATGTTGC TGTGCTTACT CTAGCCATCC TGATGTTCCT

51 GACATGGCTT CCAGAATCAC TGAGCTGTAA CAAAGCACTC TGTGCTAGTG

101 ATGTGAGCAA ATGCCTCATT CAGGAGCTCT GCCAGTGCCG GCCGGGAGAA

151 GGCAATTGCT CCTGCTGTAA GGAGTGCATG CTGTGTCTTG GGGCCCTTTG

201 GGACGAGTGC TGTGACTGTG TTGGTATGTG TAATCCTCGA AATTATAGTG

251 ACACACCTCC AACTTCAAAG AGCACAGTGG AGGAGCTGCA TGAACCGATC

301 CCTTCTCTCT TCCGGGCACT CACAGAAGGA GATACTCAGT TGAATTGGAA
```

```
-continued
351 CATCGTTTCT TTCCCTGTTG CAGAAGAACT TTCACATCAT GAGAATCTGG

401 TTTCATTTTT AGAAACTGTG AACCAGCCAC ACCACCAGAA TGTGTCTGTC

451 CCCAGCAATA ATGTTCACGC GCCTTATTCC AGTGACAAAG AACACATGTG

501 TACTGTGGTT TATTTTGATG ACTGCATGTC CATACATCAG TGTAAAATAT

551 CCTGTGAGTC CATGGGAGCA TCCAAATATC GCTGGTTTCA TAATGCCTGC

601 TGCGAGTGCA TTGGTCCAGA ATGTATTGAC TATGGTAGTA AAACTGTCAA

651 ATGTATGAAC TGCATGTTT
```

In some embodiments, TWSG polypeptides comprise a signal sequence in addition to the TWSG protein. The signal sequence can be a native signal sequence of a TWSG protein, or a signal sequence from another protein, such as a tissue plasminogen activator (TPA) signal sequence or a honey bee melittin (HBM) signal sequence.

TWSG is highly conserved in amino acid sequence across vertebrates, including human, chimpanzee, rhesus macaque, dog, cow, mouse, rat, chicken, zebrafish, and frog. See, e.g., Oelgeschlager et al., 2000, Nature 405:757-763. Ligands that bind to TWSG are also highly conserved. Accordingly, comparisons of TWSG sequences from various vertebrate organisms provide insights into residues that may be altered. Therefore, an active, variant human TWSG polypeptide may include one or more amino acids at corresponding positions from the sequence of another vertebrate TWSG polypeptide, or may include a residue that is similar to that in the human or other vertebrate sequence.

In certain embodiments, isolated fragments of TWSG polypeptides can be obtained by screening polypeptides recombinantly produced from the corresponding fragment of the nucleic acid encoding an TWSG polypeptide (e.g., SEQ ID NOs: 2 and 14). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of a TWSG polypeptide or a TWSG polypeptide ligand.

In certain embodiments, the TWSG polypeptide is a variant having an amino acid sequence that is at least 75% identical to an amino acid sequence selected from SEQ ID NOs: 1, 8, 9, or 13. In certain cases, the TWSG polypeptide has an amino acid sequence at least 80%, 85%, 90%, 91%, 92%, 93%, 94%, 95%, 96%, 97%, 98%, 99% or 100% identical to an amino acid sequence selected from SEQ ID NOs: 1, 8, 9, or 13. In certain embodiments, the TWSG polypeptide comprises, consists essentially of, or consists of, an amino acid sequence at least 80%, 85%, 90%, 95%, 97%, 98%, 99% or 100% identical to an amino acid sequence selected from SEQ ID NOs: 1, 8, 9, or 13.

In certain embodiments, the present invention contemplates making functional variants by modifying the structure of a TWSG polypeptide for such purposes as enhancing therapeutic efficacy, or stability (e.g., ex vivo shelf life and resistance to proteolytic degradation in vivo). TWSG polypeptides can also be produced by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a TWSG polypeptide results in a functional variant can be readily determined by assessing the ability of the TWSG polypeptide to produce a response in cells relative to wild-type TWSG polypeptide, or to bind to one or more ligands, such as BMP2, BMP4, BMP6, BMP7, or BMP9 as compared to wild-type TWSG polypeptide.

In certain specific embodiments, the present invention contemplates making mutations in a TWSG polypeptide such that the TWSG polypeptide has altered ligand-binding activities (e.g., binding affinity or binding specificity). In certain cases, such TWSG polypeptides have altered (elevated or reduced) binding affinity for a specific ligand. In other cases, the TWSG polypeptides have altered binding specificity for TWSG ligands.

In certain embodiments, the present invention contemplates TWSG polypeptides having specific mutations in TWSG so as to alter the glycosylation of the TWSG polypeptide. Exemplary glycosylation sites in TWSG polypeptides are illustrated in FIG. 1 (e.g., the underlined NX(S/T) sites). Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid), which is specifically recognized by appropriate cellular glycosylation enzymes. The alteration may also be made by the addition of, or substitution by, one or more serine or threonine residues to the sequence of the wild-type TWSG polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a TWSG polypeptide is by chemical or enzymatic coupling of glycosides to the TWSG polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 and in Aplin and Wriston (1981) CRC Crit. Rev. Biochem., pp. 259-306, incorporated by reference herein. Removal of one or more carbohydrate moieties present on a TWSG polypeptide may be accomplished chemically and/or enzymatically. Chemical deglycosylation may involve, for example, exposure of the TWSG polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on TWSG polypeptides can be achieved by the use of a variety of endo- and exo-glycosidases as described by Thotakura et al. (1987) Meth. Enzymol. 138: 350. The sequence of a TWSG polypeptide may be adjusted, as appropriate, depending on the type of expression system used, as mammalian, yeast, insect and plant cells may all introduce differing glycosylation patterns that can be affected by the amino acid sequence of the peptide. In general, TWSG polypeptides for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of a TWSG polypeptide, including, optionally, truncation variants; pools of combinatorial mutants are especially useful for identifying TWSG polypeptide sequences. The purpose of screening such combinatorial libraries may be to generate, for example, TWSG polypeptide variants which have altered properties, such as altered pharmacokinetics, or altered ligand binding. A variety of screening assays are provided below, and such assays may be used to evaluate variants. For example, a TWSG polypeptide variant may be screened for the ability to bind to a TWSG polypeptide, to prevent binding of a TWSG ligand to a TWSG polypeptide, or to interfere with signaling caused by a TWSG ligand.

The activity of a TWSG polypeptide or its variants may also be tested in a cell-based or in vivo assay. For example, the effect of a TWSG polypeptide variant on the expression of genes involved in hematopoiesis may be assessed. This may, as needed, be performed in the presence of one or more recombinant TWSG ligand proteins (e.g., BMP6), and cells may be transfected so as to produce a TWSG polypeptide and/or variants thereof, and optionally, a TWSG ligand. Likewise, a TWSG polypeptide may be administered to a mouse or other animal, and one or more blood measurements, such as an RBC count, hemoglobin levels, hematocrit levels, iron stores, or reticulocyte count may be assessed using art-recognized methods.

Combinatorially-derived variants can be generated which have a selective potency relative to a reference TWSG polypeptide. Such variant proteins, when expressed from recombinant DNA constructs, can be used in gene therapy protocols. Likewise, mutagenesis can give rise to variants which have intracellular half-lives dramatically different than the corresponding unmodified TWSG polypeptide. For example, the altered protein can be rendered either more stable or less stable to proteolytic degradation or other processes which result in destruction of, or otherwise inactivation of an unmodified TWSG polypeptide. Such variants, and the genes which encode them, can be utilized to alter TWSG polypeptide levels by modulating the half-life of the TWSG polypeptides. For instance, a short half-life can give rise to more transient biological effects and, when part of an inducible expression system, can allow tighter control of recombinant TWSG polypeptide levels within the cell. In an Fc fusion protein, mutations may be made in the linker (if any) and/or the Fc portion to alter the half-life of the protein.

In certain embodiments, the TWSG polypeptides of the invention may further comprise post-translational modifications in addition to any that are naturally present in the TWSG polypeptides. Such modifications include, but are not limited to, acetylation, carboxylation, glycosylation, phosphorylation, lipidation, and acylation. As a result, TWSG polypeptides may contain non-amino acid elements, such as polyethylene glycols, lipids, poly- or mono-saccharide, and phosphates. Effects of such non-amino acid elements on the functionality of a TWSG polypeptide may be tested as described herein for other TWSG polypeptide variants. When a TWSG polypeptide is produced in cells by cleaving a nascent form of the TWSG polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the TWSG polypeptides.

In certain aspects, TWSG polypeptides include fusion proteins having at least a portion of a TWSG polypeptide and one or more fusion domains. Well-known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) (SEQ ID NO: 22) fusion partners. As another example, a fusion domain may be selected so as to facilitate detection of the TWSG polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

In certain preferred embodiments, a TWSG polypeptide is fused to a domain that stabilizes the TWSG polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further increasing red blood cell levels).

As specific examples, the present disclosure provides fusion proteins comprising a TWSG polypeptide fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimeric complex of the disclosure. Optionally, the IgG1 Fc domain of SEQ ID NO: 3 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wild-type Fc domain.

An example of a native amino acid sequence that may be used for the Fc portion of human IgG1 (G1Fc) is shown below (SEQ ID NO: 3). Dotted underline indicates the hinge region, and solid underline indicates positions with naturally occurring variants. In part, the disclosure provides polypeptides comprising amino acid sequences with 80%, 85%, 90%, 95%, 96%, 97%, 98%, or 99% identity to SEQ ID NO: 3. Naturally occurring variants in G1Fc would include E134D and M136L according to the numbering system used in SEQ ID NO: 3 (see Uniprot P01857).

```
                                                              (SEQ ID NO: 3)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 4). Dotted underline indicates the hinge region and double underline indicates positions where there are data base conflicts in the sequence (according to UniProt P01859). In part, the disclosure provides polypeptides comprising amino acid sequences with 80%, 85%, 90%, 95%, 96%, 97%, 98%, or 99% identity to SEQ ID NO: 4.

```
                                                              (SEQ ID NO: 4)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 5) contains a short hinge region consisting of a single 15-residue segment, whereas the second G3Fc sequence (SEQ ID NO: 6) contains a full-length hinge region. In each case, dotted underline indicates the hinge region, and solid underline indicates positions with naturally occurring variants according to UniProt P01859. In part, the disclosure provides polypeptides comprising amino acid sequences with 80%, 85%, 90%, 95%, 96%, 97%, 98%, or 99% identity to SEQ ID NOs: 5 and 6.

```
                                                              (SEQ ID NO: 5)
  1 ESKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL
```

```
151 TCLVKGFYPS DIAVEWESSG QPENNYNTTP PMLDSDGSFF LYSKLTVDKS

201 RWQQGNIFSC SVMHEALHNR FTQKSLSLSP GK
```

(SEQ ID NO: 6)
```
  1 ELKTPLGDTT HTCPRCPEPK SCDTPPPCPR CPEPKSCDTP PPCPRCPEPK

51 SCDTPPPCPR CPAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 5, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01860]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 7). For example, see Uniprot P01861. Dotted underline indicates the hinge region. In part, the disclosure provides polypeptides comprising amino acid sequences with 80%, 85%, 90%, 95%, 96%, 97%, 98%, or 99% identity to SEQ ID NO: 7.

(SEQ ID NO: 7)
```
  1 ESKYGPPCPS CPAPEFLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

It is understood that different elements of the fusion proteins may be arranged in any manner that is consistent with the desired functionality. For example, a TWSG polypeptide may be placed C-terminal to a heterologous domain, or, alternatively, a heterologous domain may be placed C-terminal to a TWSG polypeptide. The TWSG polypeptide domain and the heterologous domain need not be adjacent in a fusion protein, and additional domains or amino acid sequences may be included C- or N-terminal to either domain or between the domains.

In certain embodiments, a TWSG fusion protein comprises an amino acid sequence as set forth in the formula A-B-C. The B portion is a TWSG polypeptide comprising the amino acid sequence corresponding to amino acids 26-223 of SEQ ID NO: 1. The A and C portions may be independently zero, one or more than one amino acids, and both the A and C portions when present are heterologous to B. The A and/or C portions may be attached to the B portion via a linker sequence. Exemplary linkers include short polypeptide linkers such as 2-10, 2-5, 2-4, 2-3 glycine residues, such as, for example, a Gly-Gly-Gly linker. Other suitable linkers are described herein above. In certain embodiments, a TWSG fusion protein comprises an amino acid sequence as set forth in the formula A-B-C, wherein A is a leader sequence, B consists of amino acids 26-223 of SEQ ID NO: 1, and C is a polypeptide portion that enhances one or more of in vivo stability, in vivo half life, uptake/administration, tissue localization or distribution, formation of protein complexes, and/or purification. In certain embodiments, a TWSG fusion protein comprises an amino acid sequence as set forth in the formula A-B-C, wherein A is a TPA leader sequence, B consists of amino acids 26-223 of SEQ ID NO: 1, and C is an immunoglobulin Fc domain. A preferred TWSG fusion protein comprises the amino acid sequence set forth in SEQ ID NO: 13.

In certain embodiments, the TWSG polypeptides of the present invention contain one or more modifications that are capable of stabilizing the TWSG polypeptides. For example, such modifications enhance the in vitro half-life of the TWSG polypeptides, enhance circulatory half-life of the TWSG polypeptides or reduce proteolytic degradation of the TWSG polypeptides. Such stabilizing modifications include, but are not limited to, fusion proteins (including, for example, fusion proteins comprising an TWSG polypeptide and a stabilizer domain), modifications of a glycosylation site (including, for example, addition of a glycosylation site to a TWSG polypeptide), and modifications of carbohydrate moiety (including, for example, removal of carbohydrate moieties from a TWSG polypeptide). In the case of fusion proteins, a TWSG polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the TWSG polypeptides, which are isolated from, or otherwise substantially free of, other proteins.

In certain embodiments, TWSG polypeptides (unmodified or modified) of the invention can be produced by a variety of art-known techniques. For example, such TWSG polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the TWSG polypeptides, fragments or variants thereof may be recombinantly produced using various expression systems (e.g., E. coli, Chinese Hamster Ovary (CHO) cells, COS cells, baculovirus) as is well known in the art. In further embodiments, the modified or unmodified TWSG polypeptides may be produced by digestion of recombinantly produced full-length TWSG polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such TWSG polypeptides may be produced from recombinantly produced full-length TWSG polypeptides such as standard techniques known in the art, such as by chemical cleavage (e.g., cyanogen bromide, hydroxylamine).

3. Nucleic Acids Encoding TWSG Polypeptides

In certain aspects, the invention provides isolated and/or recombinant nucleic acids encoding any of the TWSG polypeptides disclosed herein. SEQ ID NO: 2 encodes a naturally occurring TWSG precursor polypeptide while SEQ ID NO: 14 encodes a soluble TWSG fusion protein. The subject nucleic acids may be single-stranded or double stranded. Such nucleic acids may be DNA or RNA molecules. These nucleic acids may be used, for example, in methods for making TWSG polypeptides or as direct therapeutic agents (e.g., in a gene therapy approach).

In certain aspects, the subject nucleic acids encoding TWSG polypeptides are further understood to include nucleic acids that are variants of SEQ ID NOs: 2 and 14. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 2 and 14.

In certain embodiments, the invention provides isolated or recombinant nucleic acid sequences that are at least 80%, 85%, 90%, 91%, 92%, 93%, 94%, 95%, 96%, 97%, 98%, 99% or 100% identical to SEQ ID NO: 2 and 14. One of ordinary skill in the art will appreciate that nucleic acid sequences complementary to SEQ ID NO: 2 and 14, and variants of SEQ ID NO: 2 and 14, are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 2 and 14, complement sequence of SEQ ID NO: 2 and 14, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 2 and 14 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. In certain embodiments, the TWSG polypeptide will be encoded by an alternative nucleotide sequence. Alternative nucleotide sequences are degenerate with respect to the native TWSG nucleic acid sequence but still encode for the same fusion protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In certain preferred embodiments, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a TWSG polypeptide and operably linked to at least one regulatory sequence. Regulatory sequences are art-recognized and are selected to direct expression of the TWSG polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding a TWSG polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant TWSG polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In certain preferred embodiments, a vector will be designed for production of the subject TWSG polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wisc.). As will be apparent, the subject gene constructs can be used to cause expression of the subject TWSG polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 2 or 14) for one or more of the subject TWSG polypeptides. The host cell may be any prokaryotic or eukaryotic cell. For example, a TWSG polypeptide of the invention may be expressed in bacterial cells such as E. coli, insect cells (e.g., using a baculovirus expression system), yeast, or mammalian cells. Other suitable host cells are known to those skilled in the art.

Accordingly, the present invention further pertains to methods of producing the subject TWSG polypeptides. For example, a host cell transfected with an expression vector encoding a TWSG polypeptide can be cultured under appropriate conditions to allow expression of the TWSG polypeptide to occur. The TWSG polypeptide may be secreted and isolated from a mixture of cells and medium containing the TWSG polypeptide. Alternatively, the TWSG polypeptide may be retained cytoplasmically or in a membrane fraction and the cells harvested, lysed and the protein isolated. A cell culture includes host cells, media and other byproducts. Suitable media for cell culture are well known in the art. The subject TWSG polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the TWSG polypeptides. In certain preferred embodiments, the TWSG polypeptide is a fusion protein containing a domain which facilitates its purification.

In other embodiments, a fusion gene coding for a purification leader sequence, such as a poly-(His)/enterokinase cleavage site sequence at the N-terminus of the desired portion of the recombinant TWSG polypeptide, can allow purification of the expressed fusion protein by affinity chromatography using a $Ni^{2+}$ metal resin. The purification leader sequence can then be subsequently removed by treatment with enterokinase to provide the purified TWSG polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In other embodiments, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Screening Assays

In certain aspects, the present invention relates to the use of the subject TWSG polypeptides (e.g., soluble variant TWSG polypeptides) to identify compounds (agents) which are agonist or antagonists of TWSG polypeptides. Compounds identified through this screening can be tested to assess their ability to modulate red blood cell, hemoglobin and/or reticulocyte levels in vivo or in vitro. These compounds can be tested, for example, in animal models.

There are numerous approaches to screening for therapeutic agents for increasing red blood cell or hemoglobin levels by targeting TWSG bioactivity. In certain embodiments, high-throughput screening of compounds can be carried out to identify agents that perturb TWSG-mediated effects on a selected cell line. In certain embodiments, the assay is carried out to screen and identify compounds that specifically inhibit or reduce binding of a TWSG polypeptide to its binding partner, such as a TWSG ligand as disclosed herein (e.g., BMP2, BMP4, BMP6, BMP7, or BMP9). Alternatively, the assay can be used to identify compounds that enhance binding of a TWSG polypeptide to its binding partner such as a TWSG ligand. In further embodiments, the compounds can be identified by their ability to interact with a TWSG polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In specific embodiments, the test agent is a small organic molecule having a molecular weight of less than about 2,000 Daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TWSG polypeptide and its binding partner (e.g., a TWSG ligand).

Merely to illustrate, in an exemplary screening assay of the present invention, the compound of interest is contacted with an isolated and purified TWSG polypeptide which is ordinarily capable of binding to a TWSG binding partner, as appropriate for the intention of the assay. To the mixture of the compound and TWSG polypeptide is then added to a composition containing a TWSG binding partner. Detection and quantification of complexes between a TWSG polypeptide and its binding partner provides a means for determining the compound's efficacy at inhibiting (or potentiating) complex formation between the TWSG polypeptide and its binding partner. The efficacy of the compound can be assessed by generating dose-response curves from data obtained using various concentrations of the test compound. Moreover, a control assay can also be performed to provide a baseline for comparison. For example, in a control assay, isolated and purified TWSG ligand is added to a composition containing the TWSG polypeptide, and the formation of complexes between TWSG polypeptide and its binding partner are quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the TWSG polypeptide and its binding partner may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TWSG polypeptide or its binding partner, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a TWSG polypeptide and its binding partner. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a TWSG polypeptide and its binding partner. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two-hybrid systems to identify compounds (e.g., small molecules or peptides) that dissociate interactions between a TWSG polypeptide and its binding partner. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a TWSG polypeptide. The interaction between the compound and the TWSG polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a TWSG polypeptide. This may include a solid phase or fluid phase binding event. Alternatively, the gene encoding a TWSG polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

5. Exemplary Therapeutic Uses

In certain embodiments, the TWSG polypeptides of the present invention can be used to increase red blood cell levels in mammals such as rodents and primates, and particularly human patients. TWSG polypeptides, optionally combined with an EPO receptor activator, can be useful for treating ineffective erythropoiesis. Originally distinguished from aplastic anemia, hemorrhage, or peripheral hemolysis on the basis of ferrokinetic studies (Ricketts et al., 1978, Clin Nucl Med 3:159-164), ineffective erythropoiesis describes a diverse group of anemias in which production of mature RBCs is less than would be expected given the number of erythroid precursors (erythroblasts) present in the bone marrow (Tanno et al., 2010, Adv Hematol 2010: 358283). In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis (Aizawa et al, 2003, Am J Hematol 74:68-72), erythroblast-induced bone pathology (Di Matteo et al, 2008, J Biol Regul Homeost Agents 22:211-216), and tissue iron overload, even in the absence of therapeutic RBC transfusions (Pippard et al, 1979, Lancet 2:819-821). Thus, by boosting erythropoietic effectiveness, a TWSG polypeptide may break the aforementioned cycle and may alleviate not only the underlying anemia but also the associated complications of elevated erythropoietin levels, splenomegaly, bone pathology, and tissue iron overload. TWSG polypeptides can treat ineffective erythropoiesis, including anemia and elevated EPO levels, as well as complications such as splenomegaly, erythroblast-induced bone pathology, and iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors (Musallam et al., 2012, Cold Spring Harb Perspect Med 2:a013482). With erythroblast-induced bone pathology, attendant pathologies include low bone mineral density, osteoporosis, and bone pain (Haidar et al., 2011, Bone 48:425-432). With iron overload, attendant pathologies include hepcidin suppression and hyperabsorption of dietary iron (Musallam et al., 2012, Blood Rev 26(Suppl 1):S16-S19), multiple endocrinopathies and liver fibrosis/cirrhosis (Galanello et al., 2010, Orphanet J Rare Dis 5:11), and iron-overload cardiomyopathy (Lekawanvijit et al., 2009, Can J Cardiol 25:213-218).

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation (Schrier, 2002, Curr Opin Hematol 9:123-126). Thalassemias are collectively among the most frequent genetic disorders worldwide, with changing epidemiologic patterns predicted to contribute to a growing public health problem in both the U.S. and globally (Vichinsky, 2005, Ann NY Acad Sci 1054:18-24). Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia *intermedia* (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia (Rund et al, 2005, N Engl J Med 353: 1135-1146).

TWSG polypeptides, optionally combined with an EPO receptor activator, can be used for treating disorders of ineffective erythropoiesis besides thalassemia syndromes. Such disorders include siderblastic anemia (inherited or acquired); dyserythropoietic anemia (Types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anema, refractory megaloblastic anemia, or erythroleukemia); myelophthisic anemias, including myelofibrosis (myeloid metaplasia) and myelophthisis; congenital erythropoietic *porphyria*; and lead poisoning.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

In certain embodiments, agents of the invention may be used alone or conjointly administered with another type of therapeutic agent. As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

As shown herein, TWSG polypeptides, optionally combined with an EPO receptor activator, may be used to increase red blood cell, hemoglobin or reticulocyte levels in healthy individuals, and such TWSG polypeptides may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In some embodiments, a patient with adequate red blood cell levels is treated with a TWSG polypeptide to increase red blood cell levels, and then blood is drawn and stored for later use in transfusions.

TWSG polypeptides, optionally combined with an EPO receptor activator, disclosed herein may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dL is generally considered the lower limit of normal in the general adult population. Potential causes include bloodloss, nutritional deficits, medication reaction, various problems with the bone marrow and many diseases. More particularly, anemia has been associated with a variety of disorders that include, for example, chronic renal failure, myelodysplastic syndrome, rheumatoid arthritis, bone marrow transplantation. Anemia may also be associated with the following conditions: solid tumors (e.g., breast cancer, lung cancer, colon cancer); tumors of the lymphatic system (e.g., chronic lymphocyte leukemia, non-Hodgkins and Hodgkins lymphomas); tumors of the hematopoietic system (e.g., leukemia, myelodysplastic syndrome, multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g., some Jehovah's Witnesses); infections (e.g., malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

Myelodysplastic syndrome (MDS) is a diverse collection of hematological conditions characterized by ineffective production of myeloid blood cells and risk of transformation to acute mylogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effect due to frequency of such therapies. For example, patients who receive frequent red blood cell transfusion can have tissue and organ damage from the buildup of extra iron. TWSG polypeptides disclosed herein may be used to treat patients having MDS. In certain embodiments, patients suffering from MDS may be treated using a combination of a TWSG polypeptide in combination with an EPO receptor activator. In other embodiments, patient suffering from MDS may be treated using a combination of a TWSG polypeptide and one or more additional therapeutic agents for treating MDS including, for example, thalidomide, lenalidomide, azacitadine, decitabine, erythropoietins, deferoxamine, antihymocyte globulin, filgrastrim (G-CSF) and an erythropoietin signaling pathway agonist.

TWSG polypeptides, optionally combined with an EPO receptor activator, would be appropriate for treating anemias of hypoproliferative bone marrow, which are typically associated with little change in red blood cell (RBC) morphology. Hypoproliferative anemias include: 1) anemia of chronic disease, 2) anemia of kidney disease, and 3) anemia associated with hypometabolic states. In each of these types, endogenous erythropoietin levels are inappropriately low for the degree of anemia observed. Other hypoproliferative anemias include: 4) early-stage iron-deficient anemia, and 5) anemia caused by damage to the bone marrow. In these types, endogenous erythropoietin levels are appropriately elevated for the degree of anemia observed.

The most common type is anemia of chronic disease, which encompasses inflammation, infection, tissue injury, and conditions such as cancer, and is distinguished by both low erythropoietin levels and an inadequate response to erythropoietin in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflamatory cytokines such as interleukin-1, interferon-gamma, and tumor necrosis factor (Bron et al., 2001, Semin Oncol 28(Suppl 8):1-6). Among its effects, inflammation induces the key iron-regulatory peptide hepcidin, thereby inhibiting iron export from macrophages and generally limiting iron availability for erythropoiesis (Ganz, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity with the degree of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function (Levin et al., 1999, Am J Kidney Dis 27:347-354; Nissenson, 1992, Am J Kidney Dis 20(Suppl 1):21-24; Revicki et al., 1995, Am J Kidney Dis 25:548-554; Gafter et al., 1994, Kidney Int 45:224-231). A TWSG polypeptide, optionally combined with an EPO receptor activator, can be used to treat anemia of kidney disease.

Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. As demonstrated by the Applicants in a mouse model (see Example below), a TWSG polypeptide, optionally combined with an EPO receptor activator, can be used to speed recovery from anemia of acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and RBC transfusion as major conventional options. A TWSG polypeptide, optionally combined with an EPO receptor activator, could be used to treat chronic iron-deficiency anemias alone or in combination with conventional therapeutic approaches, particularly to treat anemias of multifactorial origin.

Hypoproliferative anemias can result from primary dysfunction or failure of the bone marrow, instead of dysfunction secondary to inflammation, infection, or cancer progression. Prominent examples would be myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). A TWSG polypeptide, optionally combined with an EPO receptor activator, can be used to treat anemia caused by chemotherapeutic agents and/or radiation therapy.

In patients who receive frequent transfusions of whole blood or red blood cells, normal mechanisms of iron homeostasis can be overwhelmed, eventually leading to toxic and potentially fatal accumulation of iron in vital tissues such as heart, liver, and endocrine glands. Regular red blood cell transfusions require exposure to various donor units of blood and hence a higher risk of alloimmunization. Difficulties with vascular access, availability of and compliance with iron chelation, and high cost are some of the reasons why it can be beneficial to limit the number of red blood cell transfusions. In some embodiments, a TWSG polypeptide may administered to a patient that has been administered one or more blood cell transfusions (whole or red blood cell transfusions). In some embodiments, the disclosure relates to methods using a TWSG polypeptide to treat, prevent, or reduce the progression rate and/or severity anemia or anemia-related disorder in patient that is blood cell transfusion-dependent. In certain aspects, a TWSG polypeptide may be used to decrease (reduce) blood cell transfusion burden in a patient with anemia or anemia-related disorder. For example, a TWSG polypeptide may be used to decrease blood cell transfusion by greater than about 30%, 40%, 50%, 60%, 70%, 80%, 90%, or 100% for 4 to 8 weeks relative to the equal time prior to the start of the TWSG polypeptide treatment in a patient with anemia or an anemia-related disorder. In some embodiments, a TWSG polypeptide may be used to decrease blood cell transfusion by greater than about 50% for 4 to 8 weeks relative to the equal time prior to the start of the TWSG polypeptide treatment in a patient with anemia or an anemia-related disorder. In certain aspects, a TWSG polypeptide may be used to decrease iron overload in a patient with anemia or anemia-related disorder. For example, a TWSG polypeptide may be used to decrease iron overload in an organ and/or tissue in a patient with anemia or an anemia-related disorder. In some embodiments, a TWSG polypeptide may be used to decrease iron overload in the spleen of a patient with anemia or an anemia-related disorder. In some embodiments, a TWSG polypeptide may be used to decrease iron overload in the liver of a patient with anemia or an anemia-related disorder. In some embodiments, a TWSG polypeptide may be used to decrease iron overload in the heart of a patient with anemia or an anemia-related disorder.

TWSG polypeptides, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, TWSG polypeptides may be used in combination (e.g., administered at the same time or different times, but generally in such a manner as to achieve overlapping pharmacologic effects) with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload (Hershko, 2006, Haematologica 91:1307-1312; Cao et al, 2011, Pediatr Rep 3(2):e17). Effective iron-chelating agents must be able to selectively bind and neutralize ferric iron, the oxidized form of non-transferrin bound iron which likely accounts for most iron toxicity through catalytic production of hydroxyl radicals and oxidation products (Esposito et al, 2003, Blood 102:2670-2677). These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) (Kalinowski et al, 2005, Pharmacol Rev 57:547-583). Effective iron-chelating agents also are relatively low molecular weight (less than 700 daltons), with solubility in both water and lipid to enable access to affected tissues. Specific examples of iron-chelating molecules are deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone (Cao et al, 2011, Pediatr Rep 3(2):e17; Galanello et al, 2010, Ann NY Acad Sci 1202:79-86).

In certain embodiments, TWSG polypeptides may be used in combination with hepcidin agonists for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis (Nemeth, 2010, Adv Hematol 2010:750643). This view is supported by beneficial effects of increased hepcidin expression in a mouse model of β-thalassemia (Gardenghi et al, 2010, J Clin Invest 120: 4466-4477).

Additionally, TWSG polypeptides may be used in combination with EPO receptor activators to achieve an increase in red blood cells at lower dose ranges. This may be beneficial in reducing the known off-target effects and risks associated with high doses of EPO receptor activators. In certain embodiments, the present invention provides methods of treating or preventing anemia in an individual in need thereof by administering to the individual a therapeutically effective amount of a TWSG polypeptide or a combination (or concomitant therapy) of a TWSG polypeptide and a EPO receptor activator. These methods may be used for therapeutic and prophylactic treatments of mammals, and particularly humans.

The TWSG polypeptides may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72(suppl 6), S36-S43; Horl et al. (2000) Nephrol Dial Transplant 15(suppl 4), 51-56; Delanty et al. (1997) Neurology 49, 686-689; Bunn (2002) N Engl J Med 346(7), 522-523).

Patients may be treated with a dosing regimen intended to restore the patient to a target hemoglobin level, usually between about 10 g/dl and about 12.5 g/dl, and typically about 11.0 g/dl (see also Jacobs et al. (2000) Nephrol Dial Transplant 15, 15-19), although lower target levels may cause fewer cardiovascular side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

In certain embodiments, the present invention provides methods for managing a patient that has been treated with, or is a candidate to be treated with, a TWSG polypeptide by measuring one or more hematologic parameters in the patient. The hematologic parameters may be used to evaluate appropriate dosing for a patient who is a candidate to be treated with a TWSG polypeptide, to monitor the hematologic parameters during treatment with a TWSG polypeptide, to evaluate whether to adjust the dosage during treatment with a TWSG polypeptide, and/or to evaluate an appropriate maintenance dose of a TWSG polypeptide. If one or more of the hematologic parameters are outside the normal level, dosing with a TWSG polypeptide may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In some embodiments, if one or more hematologic parameters are outside the normal range, or on the high side of normal, in a patient who is a candidate to be treated with a TWSG polypeptide then onset of administration of the TWSG polypeptide may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the TWSG polypeptide may be delayed until the levels have returned to a normal or acceptable level.

In certain embodiments, if one or more hematologic parameters are outside the normal range, or on the high side of normal, in a patient who is a candidate to be treated with a TWSG polypeptide then the onset of administration may be not be delayed. However, the dosage amount or frequency of dosing of the TWSG polypeptide may be set at an amount that would reduce the risk of an unacceptable increase in the hematologic parameters arising upon administration of the TWSG polypeptide. Alternatively, a therapeutic regimen may be developed for the patient that combines a TWSG polypeptide with a therapeutic agent that addresses the undesirable level of the hematologic parameter. For example, if the patient has elevated blood pressure, then a therapeutic regimen involving administration of a TWSG polypeptide and a blood pressure lowering agent may be designed. For a patient having lower than desired iron stores, a therapeutic regimen of a TWSG polypeptide and iron supplementation may be developed.

In some embodiments, baseline parameter(s) for one or more hematologic parameters may be established for a patient who is a candidate to be treated with a TWSG polypeptide and an appropriate dosing regimen establish for that patient based on the baseline value(s). Alternatively, established baseline parameters based on a patient's medical history could be used to inform an appropriate TWSG polypeptide dosing regimen for a patient. For example, if a healthy patient has an established baseline blood pressure reading that is above the defined normal range it may not be necessary to bring the patient's blood pressure into the range that is considered normal for the general population prior to treatment with the TWSG polypeptide. A patient's baseline values for one or more hematologic parameters prior to treatment with a TWSG polypeptide may also be used as the relevant comparative values for monitoring any changes to the hematologic parameters during treatment with the TWSG polypeptide.

In certain embodiments, one or more hematologic parameters are measured in patients who are being treated with a TWSG polypeptide. The hematologic parameters may be used to monitor the patient during treatment and permit adjustment or termination of the dosing with the TWSG polypeptide or additional dosing with another therapeutic agent. For example, if administration of a TWSG polypeptide results in an increase in blood pressure, red blood cell level, or hemoglobin level, or a reduction in iron stores, then the dose of the TWSG polypeptide may be reduced in amount or frequency in order to decrease the effects of the TWSG polypeptide on the one or more hematologic parameters. If administration of a TWSG polypeptide results in a change in one or more hematologic parameters that is adverse to the patient, then the dosing of the TWSG polypeptide may be terminated either temporarily, until the hematologic parameter(s) return to an acceptable level, or permanently. Similarly, if one or more hematologic parameters are not brought within an acceptable range after reducing the dose or frequency of administration of the TWSG polypeptide then the dosing may be terminated. As an alternative, or in addition to, reducing or terminating the dosing with the TWSG polypeptide, the patient may be dosed with an additional therapeutic agent that addresses the undesirable level in the hematologic parameter(s), such as, for example, a blood pressure lowering agent or an iron supplement. For example, if a patient being treated with a TWSG polypeptide has elevated blood pressure, then dosing with the TWSG polypeptide may continue at the same level and a blood pressure lowering agent is added to the treatment regimen, dosing with the TWSG polypeptide may be reduce (e.g., in amount and/or frequency) and a blood pressure lowering agent is added to the treatment regimen, or dosing with the TWSG polypeptide may be terminated and the patient may be treated with a blood pressure lowering agent.

6. Pharmaceutical Compositions

In certain embodiments, compounds (e.g., TWSG polypeptides) of the present invention are formulated with a pharmaceutically acceptable carrier. For example, a TWSG polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally, e.g., using an implant or device. When administered, the therapeutic composition for use in this invention may be in any physiologically acceptable form, such as in a pyrogen-free composition. Therapeutically useful agents other than the TWSG polypeptides which may also optionally be included in the composition as described above, may be administered simultaneously or sequentially with the subject compounds (e.g., TWSG polypeptides) in the methods of the invention.

Typically, compounds will be administered parenterally. Pharmaceutical compositions suitable for parenteral administration may comprise one or more TWSG polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone marrow). In certain embodiments, compositions of the present invention may include a matrix capable of delivering one or more therapeutic compounds (e.g., TWSG polypeptides) to a target tissue site (e.g., bone marrow), providing a structure for the developing tissue and optimally capable of being resorbed into the body. For example, the matrix may provide slow release of the TWSG polypeptides. Such matrices may be formed of materials suitable for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., TWSG polypeptides). The various factors include, but are not limited to, the patient's red blood cell count, hemoglobin level or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

In certain embodiments, the present invention also provides gene therapy for the in vivo production of TWSG polypeptides. Such therapy would achieve its therapeutic effect by introduction of the TWSG polynucleotide sequences into cells or tissues having the disorders as listed above. Delivery of TWSG polynucleotide sequences can be achieved using a recombinant expression vector such as a chimeric virus or a colloidal dispersion system. Preferred for therapeutic delivery of TWSG polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the TWSG polynucleotide.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TWSG polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of Human TWSG-Fc Fusion Protein

Applicants constructed a soluble TWSG fusion protein (TWSG-Fc) in which full-length human TWSG (FIG. 1, SEQ ID NO: 8) was attached at its C-terminus to a human IgG1 Fc domain (SEQ ID NO: 3) with a minimal linker. TWSG-Fc (FIG. 2, SEQ ID NO: 9) was initially expressed by transient transfection in COS cells, as were N-glycosylation variants of TWSG-Fc (see below). In brief, COS cells (ATCC®) were transfected overnight with plasmid encoding TWSG-Fc using FuGENE® 6 transfection reagent (Promega). The next day, cells were washed with phosphate-buffered saline, and serum-free medium was added. After incubation for 72 h, the COS-conditioned medium was harvested, filtered, and loaded on a MabSelect SuRe column (GE Healthcare, UK). Fusion protein was eluted with 0.1 M glycine (pH 3.0), and the eluted fractions were immediately neutralized by addition 1 M Tris (pH 8.0) in a 1:10 ratio. Protein was quantitated using a NanoDrop™ spectrophotometer (Thermo Fisher Scientific, Waltham, MA).

CHO cells were transfected by standard methods with plasmid encoding TWSG-Fc and containing a ubiquitous chromatin opening element (UCOE) to facilitate protein expression. See, e.g., Cytotechnology (2002) 38:43-46. Pools were selected in methotrexate (MTX) at concentrations of 10 nM, 20 nM, and 50 nM. The 50 nM MTX pool yielded the highest expression level, so a dilution clone was obtained from this pool and adapted to serum-free suspension growth to generate conditioned media for purification.

Three different leader sequences may be used:
(i) the leader sequence for Honey bee mellitin (HBML): MKFLVNVALVFMVVYISYIYA (SEQ ID NO: 10)
(ii) the leader sequence for Tissue plasminogen activator (TPA): MDAMKRGLCCVLLLCGAVFVSP (SEQ ID NO: 11)
(iii) the leader sequence for Native human TWSG: MKLHYVAVLTLAILMFLTWLPESLS (SEQ ID NO: 12)

The selected form of TWSG-Fc uses the TPA leader, has the unprocessed amino acid sequence shown in FIG. 3 (SEQ ID NO: 13), and is encoded by the nucleotide sequence shown in FIG. 4 (SEQ ID NO: 14). Applicants also envision an alternative TWSG-hFc sequence with or without TPA leader comprising a different hFc domain (for example, SEQ ID NOs: 4, 5, 6, or 7, or a chimeric Fc domain from different IgG origins, such as chimeric G2/G4 constant regions)

attached to at least one end of the C-terminus and N-terminus of human TWSG by a minimal linker.

Purification of Fusion Protein Derived from CHO Cells

Human TWSG-Fc expressed in CHO cells was purified as follows for subsequent characterization by surface plasmon resonance and reporter gene assays. Conditioned medium containing hTWSG-hFc was concentrated, filtered, and loaded on a MAb SelectSuRe column previously equilibrated with PBS. Resin was then washed with PBS, and the protein was eluted with 0.1M glycine pH 3.5. Fractions containing protein were neutralized with 5% (v/v) 1M Tris pH 8.0. The elution pool was loaded on a Q Sepharose FF 10 mL column (GE Healthcare) previously equilibrated with buffers A (50 mM Tris pH 8.0) and B (50 mM Tris, 1M NaCl pH 8.0). A wash was performed at 10% B (100 mM NaCl), followed by elution at 20% B (200 mM NaCl). Protein was further processed over HiLoad™ 26/60 Superdex (GE Healthcare) equilibrated in PBS containing 50 mM arginine (pH 7.22). Fractions were evaluated by analytical size-exclusion chromatography, and those containing over 90% monomer were pooled, concentrated, and characterized. Purity of samples was evaluated by analytical size-exclusion chromatography and SDS-PAGE with Coomassie staining. Analysis indicated that the mature protein has an N-terminal sequence of CNKAL (SEQ ID NO: 15).

Example 2. Ligand Binding to Murine TWSG and Human TWSG-Fc

Previous studies have determined that TWSG, or its nonmammalian homolog Tsg, binds with high affinity to BMP2, BMP4, and BMP7 (Oelgeschläger et al., 2000, Nature 405:757-763; Scott et al., 2001, Nature 410:475-478; Chang et al., 2001, Nature 410:483-487). Since these studies have not systematically evaluated TWSG (or Tsg) binding to other TGFβ superfamily ligands, Applicants used surface plasmon resonance to investigate and characterize such binding. In an initial qualitative screen, recombinant murine TWSG (mTWSG; R&D Systems, Minneapolis, MN) was covalently immobilized on a BIACORE™ CM5 chip, and more than 30 ligands generated in-house or obtained from R&D Systems were injected individually over the captured mTWSG to characterize their degree of binding at room temperature. Based on the results of this screen, Applicants subjected selected ligands to quantitative characterization of binding to human TWSG fusion protein at physiologic temperature. For this analysis, TWSG-Fc was expressed in CHO cells, purified as described in Example 1, captured on a BIACORE™ chip with anti-Fc antibody, and tested by surface plasmon resonance with the following ligands at 37° C.

| Ligand* | $k_a$ ($10^6$ M$^{-1}$s$^{-1}$) | $k_d$ ($10^{-3}$ s$^{-1}$) | $K_D$ (nM) |
| --- | --- | --- | --- |
| BMP4 | 1.9 | 1.4 | 0.23 |
| BMP6 | 8.2 | 1.9 | 0.23 |
| BMP2 | 7.4 | 2.2 | 0.30 |
| BMP7 | 4.8 | 1.6 | 0.33 |
| BMP9 | 66.0 | 25.0 | 4.4 |
| BMP10 | — | — | No binding |

*All ligands (R&D Systems) were human.

As shown in the table above, human TWSG-Fc can bind with sub-nanomolar affinity to four TGFβ superfamily ligands (BMP2, BMP4, BMP6, BMP7). Although TWSG-Fc exhibited low nanomolar affinity for BMP9 at equilibrium, the off-rate ($k_d$) for BMP9 was at least an order of magnitude faster than for any of the other ligands shown, corresponding to a mean residence time for the ligand-receptor complex of approximately 1 minute. This relatively short residence time likely explains the inability of TWSG-Fc fusion protein to inhibit BMP9 signaling in a cell-based assay (see Example 3). Even when expressed stably in CHO cells, TWSG-Fc displayed no binding to the closely related ligand BMP10, as determined by surface plasmon resonance.

The affinity of murine TWSG for BMP2 and BMP4 has been reported to vary with its glycosylation status (Billington Jr. et al., 2011, Front Physiol 2:59). Therefore, Applicants generated several glycosylation variants of hTWSG-hFc by mutating existing sites (FIG. 3) of N-linked glycosylation in the hTWSG sequence, both individually and in combination, and expressing the constructs transiently in COS cells. Unlike reports of murine variants, ligand binding properties of these human glycosylation variants as determined by surface plasmon resonance and reporter gene assay were found to be similar to that of wild-type human TWSG-Fc.

Example 3. Inhibition of Ligand Signaling by TWSG-Fc in Cell-Based Assays

Reporter gene assays were used to determine the ability of human TWSG-Fc to inhibit signaling by BMP2, BMP4, BMP6, BMP7, BMP9, and BMP10. These assays are based on human glioblastoma (T98G) or hepatocellular carcinoma (HepG2) cell lines transfected with a pGL3 BRE (BMP response element) reporter plasmid (Korchynskyi et al., 2002, J Biol Chem 277: 4883-4891) as well as a Renilla reporter plasmid (pRLCMV) to control for transfection efficiency. BMP response elements from the Id1 promoter are present in the promoter of the pGL3 BRE reporter plasmid, so this vector is of general use for factors signaling through Smad1 and Smad5.

On the first day of the assay, T98G cells (ATCC®: CRL-1690™) or HepG2 cells (ATCC®: HB-8065™) were distributed in 48-well plates at 8.5×10⁴ cells per well or 12.5×10⁴ cells per well, respectively. On the second day, a solution containing 10 μg pGL3 BRE, 100 ng pRLCMV, 30 μl Fugene HD (Roche Applied Science, DE), and 970 μl OptiMEM™ (Invitrogen) was preincubated for 30 min, then added to assay buffer consisting of either Eagle's minimum essential medium, ATCC® (T98G), or McCoy's 5A medium, Life Technologies® (HepG2), supplemented with 0.1% BSA. The mixture was applied to the plated cells (500 μl/well) for incubation overnight at 37° C.

On the third day, medium was removed, and cells were incubated overnight at 37° C. with a mixture of ligands and inhibitors prepared as described below. TWSG-Fc was serially diluted in 200 μl volumes of assay buffer using a 48-well plate. An equal volume of assay buffer containing the test ligand was added to obtain a final ligand concentration equal to the $EC_{50}$ determined previously. Human BMP2, BMP4, BMP6, BMP7, BMP9, and BMP10 were obtained from R&D Systems. Test solutions were incubated at 37° C. for 30 minutes, then 250 μl of the mixture was added to all wells. Each concentration of test article was determined in duplicate. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

These assays were used to evaluate the ability of TWSG-Fc to inhibit cell signaling mediated by BMPs that applicants identified by surface plasmon resonance as high-affinity binders. TWSG-Fc used in these assays was expressed in CHO cells and purified as described above.

| Ligand | $IC_{50}$ ng/ml | nM |
|---|---|---|
| BMP7 | 143 | 1.5 |
| BMP4 | 208 | 2.2 |
| BMP6 | 351 | 3.7 |
| BMP2 | 2960 | 31 |
| BMP9 | ND (>3000) | ND (>31) |
| BMP10 | ND (>3000) | ND (>31) |

Values are the means of two separate experiments.
ND, not determined due to weakness of inhibition.

TWSG-hFc displayed approximately equal potency as an inhibitor of BMP4, BMP6, and BMP7, with $IC_{50}$ values in the low nanomolar range, whereas it was an order of magnitude less potent at inhibiting BMP2. As expected from surface plasmon resonance analysis, TWSG-Fc did not appreciably inhibit signaling by BMP9 or BMP10.

Example 4. Stimulatory Effect of TWSG-Fc on Iron and Erythrocyte Levels in Mice

Inflammation associated with chronic diseases, autoimmune diseases, and infection can promote anemia, for which there are limited treatment options (Roy, 2010, Hematology Am Soc Hematol Educ Program, 2010:276-80; Kwaan, 2011, Infect Disord Drug Targets 11:40-44). As demonstrated by a transgenic mouse model (Roy et al., 2007, Blood 109:4038-4044), elevated hepcidin production is now considered the primary cause of anemia of inflammation (Roy, 2010, Hematology Am Soc Hematol Educ Program, 2010: 276-80; Ganz et al., 2012, Biochim Biophys Acta 1823: 1434-1443). BMP6, in turn, has been identified as a key endogenous regulator of hepcidin expression (Camaschella, 2009, Nat Genet 41:386-388; Meynard et al., 2009, Nat Genet 41:478-481; Andriopoulos et al., 2009, Nat Genet 41:482-487).

Figure 6:
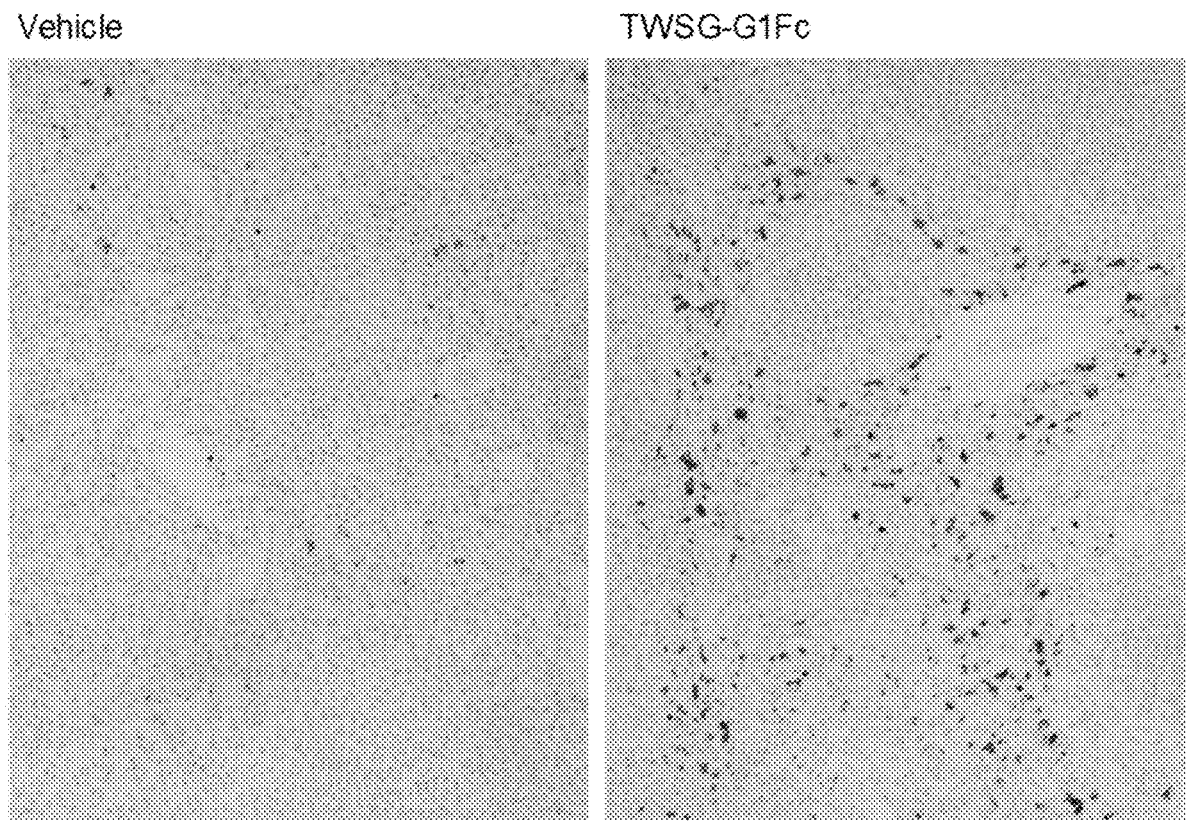
FIG. 6 shows the effect of human TWSG-Fc (labeled as "TWSG-G1Fc"; right panel) vs. vehicle control (left panel) on iron accumulation in mouse spleen as determined by microscopy with Perls' Prussian blue staining. Spleen sections from wild-type mice treated with TWSG-Fc for 4 weeks contained numerous deposits of iron reaction product spread across regions of active erythropoiesis known as red pulp (right panel). Little or no staining was present in spleen sections from vehicle-treated mice (left panel). Magnification, 200×.

Given the ability of human TWSG-Fc to inhibit signaling mediated by BMP6 in particular, Applicants investigated the effect of human TWSG-Fc on iron levels and red blood cell indices in wild-type mice. Eight-week-old C57BL/6 mice (n=5 per group) were treated intraperitoneally with TWSG-Fc (10 mg/kg) or vehicle (phosphate-buffered saline containing 50 mM arginine) either daily for 1 week or three times per wk for 4 week. Compared with vehicle, treatment with TWSG-Fc for 1 week significantly increased serum iron by 12% (n=5 per group) (FIG. 5). Four weeks treatment with TWSG-Fc markedly increased iron levels in spleen (FIG. 6) but not other tissues, indicative of upregulated erythropoiesis in spleen. As shown in FIG. 6, spleen sections from wild-type mice treated with TWSG-Fc for 4 weeks contained numerous deposits of iron reaction product spread across regions of active erythropoiesis known as red pulp (right panel, showing the Prussian blue staining under microscope). Little or no staining was present in spleen sections from vehicle-treated mice (FIG. 6, left panel). Consistent with this finding, treatment with TWSG-Fc for 4 weeks significantly increased red cell count and hemoglobin concentration (FIG. 7). As shown in FIG. 7, compared to vehicle, treatment of wild-type mice with TWSG-Fc for 4 weeks increased RBC count by 15% (FIG. 7A) and hemoglobin concentration by 12% (FIG. 7B). In these same mice, no effects of TWSG-Fc treatment were observed on bone mineral density, as determined by dual energy X-ray absorptiometry, or fluid mass, fat mass, or lean body mass, as determined by nuclear magnetic resonance. This effect profile contrasts with that of ALK3-Fc fusion proteins, which bind with highest affinity to BMP2 and BMP4 and markedly stimulate bone growth in vivo (U.S. Pat. No. 8,338,377).

Taken together, these results show that TWSG-Fc exerts stimulatory effects on iron levels and RBC indices in vivo that are consistent with its ability to inhibit BMP6 in cell-based assays. Applicants hypothesize that these effects of TWSG-Fc are mediated by reduced BMP6-dependent hepatic expression of hepcidin and reduced circulating hepcidin concentrations. Thus, TWSG fusion proteins such as TWSG-Fc might be useful for treating anemia of inflammation in patients in need thereof.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

SEQUENCE LISTING

```
Sequence total quantity: 22
SEQ ID NO: 1            moltype = AA  length = 223
FEATURE                 Location/Qualifiers
source                  1..223
                        mol_type = protein
                        organism = Homo sapiens
SEQUENCE: 1
MKLHYVAVLT LAILMFLTWL PESLSCNKAL CASDVSKCLI QELCQCRPGE GNCSCCKECM   60
LCLGALWDEC CDCVGMCNPR NYSDTPPTSK STVEELHEPI PSLFRALTEG DTQLNWNIVS  120
FPVAEELSHH ENLVSFLETV NQPHHQNVSV PSNNVHAPYS SDKEHMCTVV YFDDCMSIHQ  180
CKISCESMGA SKYRWFHNAC CECIGPECID YGSKTVKCMN CMF                    223

SEQ ID NO: 2            moltype = DNA  length = 669
FEATURE                 Location/Qualifiers
```

-continued

```
source                  1..669
                        mol_type = genomic DNA
                        organism = Homo sapiens
SEQUENCE: 2
atgaagttac actatgttgc tgtgcttact ctagccatcc tgatgttcct gacatggctt    60
ccagaatcac tgagctgtaa caaagcactc tgtgctagtg atgtgagcaa atgcctcatt   120
caggagctct gccagtgccg gccgggagaa ggcaattgct cctgctgtaa ggagtgcatg   180
ctgtgtcttg ggcccttTg ggacgagtgc tgtgactgtg ttggtatgtg taatcctcga   240
aattatagtg acacacctcc aacttcaaag agcacagtgg aggagctgca tgaaccgatc   300
ccttctctct tccgggcact cacagaagga gatactcagt tgaattggaa catcgtttct   360
ttccctgttg cagaagaact ttcacatcat gagaatctgg tttcattttt agaaactgtg   420
aaccagccac accaccagaa tgtgtctgtc cccagcaata atgttcacgc gccttattcc   480
agtgacaaag aacacatgtg tactgtggtt tattttgatg actgcatgtc catacatcag   540
tgtaaaatat cctgtgagtc catgggagca tccaaatatc gctggtttca taatgcctgc   600
tgcgagtgca ttggtccaga atgattgac tatggtagta aaactgtcaa atgtatgaac   660
tgcatgttt                                                           669

SEQ ID NO: 3            moltype = AA  length = 225
FEATURE                 Location/Qualifiers
source                  1..225
                        mol_type = protein
                        organism = Homo sapiens
SEQUENCE: 3
THTCPPCPAP ELLGGPSVFL FPPKPKDTLM ISRTPEVTCV VVDVSHEDPE VKFNWYVDGV    60
EVHNAKTKPR EEQYNSTYRV VSVLTVLHQD WLNGKEYKCK VSNKALPAPI EKTISKAKGQ   120
PREPQVYTLP PSREEMTKNQ VSLTCLVKGF YPSDIAVEWE SNGQPENNYK TTPPVLDSDG   180
SFFLYSKLTV DKSRWQQGNV FSCSVMHEAL HNHYTQKSLS LSPGK                   225

SEQ ID NO: 4            moltype = AA  length = 223
FEATURE                 Location/Qualifiers
source                  1..223
                        mol_type = protein
                        organism = Homo sapiens
SEQUENCE: 4
VECPPCPAPP VAGPSVFLFP PKPKDTLMIS RTPEVTCVVV DVSHEDPEVQ FNWYVDGVEV    60
HNAKTKPREE QFNSTFRVVS VLTVVHQDWL NGKEYKCKVS NKGLPAPIEK TISKTKGQPR   120
EPQVYTLPPS REEMTKNQVS LTCLVKGFYP SDIAVEWESN GQPENNYKTT PPMLDSDGSF   180
FLYSKLTVDK SRWQQGNVFS CSVMHEALHN HYTQKSLSLS PGK                     223

SEQ ID NO: 5            moltype = AA  length = 232
FEATURE                 Location/Qualifiers
source                  1..232
                        mol_type = protein
                        organism = Homo sapiens
SEQUENCE: 5
EPKSCDTPPP CPRCPAPELL GGPSVFLFPP KPKDTLMISR TPEVTCVVVD VSHEDPEVQF    60
KWYVDGVEVH NAKTKPREEQ YNSTFRVVSV LTVLHQDWLN GKEYKCKVSN KALPAPIEKT   120
ISKTKGQPRE PQVYTLPPSR EEMTKNQVSL TCLVKGFYPS DIAVEWESSG QPENNYNTTP   180
PMLDSDGSFF LYSKLTVDKS RWQQGNIFSC SVMHEALHNR FTQKSLSLSP GK           232

SEQ ID NO: 6            moltype = AA  length = 279
FEATURE                 Location/Qualifiers
source                  1..279
                        mol_type = protein
                        organism = Homo sapiens
SEQUENCE: 6
ELKTPLGDTT HTCPRCPEPK SCDTPPPCPR CPEPKSCDTP PPCPRCPEPK SCDTPPPCPR    60
CPAPELLGGP SVFLFPPKPK DTLMISRTPE VTCVVVDVSH EDPEVQFKWY VDGVEVHNAK   120
TKPREEQYNS TFRVVSVLTV LHQDWLNGKE YKCKVSNKAL PAPIEKTISK TKGQPREPQV   180
YTLPPSREEM TKNQVSLTCL VKGFYPSDIA VEWESSGQPE NNYNTTPPML DSDGSFFLYS   240
KLTVDKSRWQ QGNIFSCSVM HEALHNRFTQ KSLSLSPGK                          279

SEQ ID NO: 7            moltype = AA  length = 229
FEATURE                 Location/Qualifiers
source                  1..229
                        mol_type = protein
                        organism = Homo sapiens
SEQUENCE: 7
ESKYGPPCPS CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK               229

SEQ ID NO: 8            moltype = AA  length = 198
FEATURE                 Location/Qualifiers
source                  1..198
                        mol_type = protein
                        organism = Homo sapiens
SEQUENCE: 8
```

```
CNKALCASDV SKCLIQELCQ CRPGEGNCSC CKECMLCLGA LWDECCDCVG MCNPRNYSDT     60
PPTSKSTVEE LHEPIPSLFR ALTEGDTQLN WNIVSFPVAE ELSHHENLVS FLETVNQPHH    120
QNVSVPSNNV HAPYSSDKEH MCTVVYFDDC MSIHQCKISC ESMGASKYRW FHNACCECIG    180
PECIDYGSKT VKCMNCMF                                                  198

SEQ ID NO: 9           moltype = AA  length = 427
FEATURE                Location/Qualifiers
source                 1..427
                       mol_type = protein
                       organism = Homo sapiens
SEQUENCE: 9
CNKALCASDV SKCLIQELCQ CRPGEGNCSC CKECMLCLGA LWDECCDCVG MCNPRNYSDT     60
PPTSKSTVEE LHEPIPSLFR ALTEGDTQLN WNIVSFPVAE ELSHHENLVS FLETVNQPHH    120
QNVSVPSNNV HAPYSSDKEH MCTVVYFDDC MSIHQCKISC ESMGASKYRW FHNACCECIG    180
PECIDYGSKT VKCMNCMFTG GGTHTCPPCP APELLGGPSV FLFPPKPKDT LMISRTPEVT    240
CVVVDVSHED PEVKFNWYVD GVEVHNAKTK PREEQYNSTY RVVSVLTVLH QDWLNGKEYK    300
CKVSNKALPA PIEKTISKAK GQPREPQVYT LPPSREEMTK NQVSLTCLVK GFYPSDIAVE    360
WESNGQPENN YKTTPPVLDS DGSFFLYSKL TVDKSRWQQG NVFSCSVMHE ALHNHYTQKS    420
LSLSPGK                                                              427

SEQ ID NO: 10          moltype = AA  length = 21
FEATURE                Location/Qualifiers
source                 1..21
                       mol_type = protein
                       organism = Apis mellifera
SEQUENCE: 10
MKFLVNVALV FMVVYISYIY A                                               21

SEQ ID NO: 11          moltype = AA  length = 22
FEATURE                Location/Qualifiers
source                 1..22
                       mol_type = protein
                       organism = Homo sapiens
SEQUENCE: 11
MDAMKRGLCC VLLLCGAVFV SP                                              22

SEQ ID NO: 12          moltype = AA  length = 25
FEATURE                Location/Qualifiers
source                 1..25
                       mol_type = protein
                       organism = Homo sapiens
SEQUENCE: 12
MKLHYVAVLT LAILMFLTWL PESLS                                           25

SEQ ID NO: 13          moltype = AA  length = 452
FEATURE                Location/Qualifiers
source                 1..452
                       mol_type = protein
                       organism = Homo sapiens
SEQUENCE: 13
MDAMKRGLCC VLLLCGAVFV SPGASCNKAL CASDVSKCLI QELCQCRPGE GNCSCCKECM     60
LCLGALWDEC CDCVGMCNPR NYSDTPPTSK STVEELHEPI PSLFRALTEG DTQLNWNIVS    120
FPVAEELSHH ENLVSFLETV NQPHHQNVSV PSNNVHAPYS SDKEHMCTVV YFDDCMSIHQ    180
CKISCESMGA SKYRWFHNAC CECIGPECID YGSKTVKCMN CMFTGGGTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 14          moltype = DNA  length = 1356
FEATURE                Location/Qualifiers
source                 1..1356
                       mol_type = genomic DNA
                       organism = Homo sapiens
SEQUENCE: 14
atggatgcaa tgaagagagg gctctgctgt gtgctgctgc tgtgtggagc agtcttcgtt     60
tcgcccggcg ccagctgtaa caaagcactc tgtgctagtg atgtgagcaa atgcctcatt    120
caggagctct gccagtgccg gccgggagaa ggcaattgct cctgctgtaa ggagtgcatg    180
ctgtgtcttg gggccctttg ggacgagtgc tgtgactgtg taatgtgcaa taatcctcga    240
aattatagtg acacacctcc aacttcaaag agcacagtgg aggagctgca tgaaccgatc    300
ccttctctct tccgggcact cacagaagga gatactcagt tgaattggaa catcgtttct    360
ttccctgttg cagaagaact ttcacatcat gagaatctgg tttcattttt agaaactgtg    420
aaccagccac accaccagaa tgtgtctgtc ccagcaata atgttcacgc gccttattcc    480
agtgacaaag aacacatgtg tactgtggtt tattttgatg actgcatgtc catacatcag    540
tgtaaaatat cctgtgagtc catgggagca tccaaatatc gctggtttca taatgcctac    600
tgcgagtgca ttggtccaga atgtattgac tatggtagta aaactgtcaa atgtatgaac    660
tgcatgttta ccggtggtgg aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
```

```
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagccccat cgagaaaacc   1020
atctccaaag ccaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200
cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                              1356

SEQ ID NO: 15         moltype = AA  length = 5
FEATURE               Location/Qualifiers
source                1..5
                      mol_type = protein
                      organism = Homo sapiens
SEQUENCE: 15
CNKAL                                                                      5

SEQ ID NO: 16         moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 16
TGGG                                                                       4

SEQ ID NO: 17         moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 17
SGGG                                                                       4

SEQ ID NO: 18         moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 18
TGGGG                                                                      5

SEQ ID NO: 19         moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 19
SGGGG                                                                      5

SEQ ID NO: 20         moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 20
GGGGS                                                                      5

SEQ ID NO: 21         moltype = AA  length = 4
FEATURE               Location/Qualifiers
REGION                1..4
                      note = Description of Artificial Sequence: Synthetic peptide
source                1..4
                      mol_type = protein
                      organism = synthetic construct
SEQUENCE: 21
GGGG                                                                       4

SEQ ID NO: 22         moltype = AA  length = 6
```

| FEATURE | Location/Qualifiers |
|---|---|
| REGION | 1..6<br>note = Description of Artificial Sequence: Synthetic 6xHis tag |
| source | 1..6<br>mol_type = protein<br>organism = synthetic construct |

SEQUENCE: 22

HHHHHH                                                                       6

We claim:

1. A method of treating anemia in a subject, comprising administering to the subject a fusion protein comprising a Twisted Gastrulation (TWSG) polypeptide and a fragment crystallizable region (Fc) polypeptide, wherein the TWSG polypeptide comprises an amino acid sequence at least 95% identical to the amino acid sequence of SEQ ID NO: 8.

2. The method of claim 1, wherein the fusion protein binds to bone morphogenetic protein 6 (BMP6) with sub-nanomolar affinity.

3. The method of claim 1, wherein the fusion protein is a homodimer.

4. The method of claim 1, wherein the TWSG polypeptide comprises the amino acid sequence of SEQ ID NO: 8.

5. The method of claim 1, wherein the Fc polypeptide comprises an amino acid sequence at least 95% identical to the amino acid sequence of SEQ ID NO: 3, 4, 5, 6, or 7.

6. The method of claim 1, wherein the fusion protein further comprises a linker between the TWSG polypeptide and the Fc polypeptide, and wherein the linker comprises the amino acid sequence of SEQ ID NO: 16, 17, 18, 19, 20, 21, or GGG.

7. The method of claim 1, wherein the fusion protein comprises the amino acid sequence of SEQ ID NO: 9 or 13.

8. The method of claim 1, wherein the anemia is inherited anemia, acquired anemia, anemia of chronic disease, anemia of chronic inflammation, dyserythropoietic anemia Type I, dyserythropoietic anemia Type II, sickle cell anemia, hereditary spherocytosis, pyruvate kinase deficiency-related anemia, or megaloblastic anemia.

9. A method of increasing red blood cell level and/or hemoglobin level, or reducing blood transfusion-dependence (TD), in a subject, comprising administering to the subject a fusion protein comprising a Twisted Gastrulation (TWSG) polypeptide and a fragment crystallizable region (Fc) polypeptide, wherein the fusion protein comprises the amino acid sequence of SEQ ID NO: 9 or 13.

10. The method of claim 9, wherein the fusion protein binds to bone morphogenetic protein 6 (BMP6) with sub-nanomolar affinity.

11. A method of inhibiting BMP signaling in a cell, tissue, or organ of a subject, comprising administering to the subject a fusion protein comprising a Twisted Gastrulation (TWSG) polypeptide and a fragment crystallizable region (Fc) polypeptide, wherein the fusion protein comprises the amino acid sequence of SEQ ID NO: 9 or 13.

12. The method of claim 11, wherein the fusion protein binds to bone morphogenetic protein 6 (BMP6) with sub-nanomolar affinity.

* * * * *